US007243030B2

(12) United States Patent
Reeve et al.

(10) Patent No.: US 7,243,030 B2
(45) Date of Patent: Jul. 10, 2007

(54) METHODS, SYSTEMS AND COMPUTER PROGRAMS FOR DECONVOLVING THE SPECTRAL CONTRIBUTION OF CHEMICAL CONSTITUENTS WITH OVERLAPPING SIGNALS

(75) Inventors: Russell Reeve, Apex, NC (US); Elias Jeyarajah, Raleigh, NC (US); Dennis Bennett, Shorewood, WI (US)

(73) Assignee: LipoScience, Inc., Raleigh, NC (US)

( * ) Notice: Subject to any disclaimer, the term of this patent is extended or adjusted under 35 U.S.C. 154(b) by 456 days.

(21) Appl. No.: 10/691,103

(22) Filed: Oct. 22, 2003

(65) Prior Publication Data
US 2004/0098208 A1 May 20, 2004

Related U.S. Application Data

(60) Provisional application No. 60/421,177, filed on Oct. 25, 2002.

(51) Int. Cl.
*G06F 19/00* (2006.01)
(52) U.S. Cl. ........................................ 702/19; 600/410
(58) Field of Classification Search ................ 702/18, 702/21, 27, 32, 179, 196–197; 324/307–312; 600/410, 425
See application file for complete search history.

(56) References Cited

U.S. PATENT DOCUMENTS

| 4,933,844 | A | | 6/1990 | Otvos | |
|---|---|---|---|---|---|
| 5,343,389 | A | | 8/1994 | Otvos | |
| 5,572,125 | A | * | 11/1996 | Dunkel | ........................ 324/307 |
| 6,452,179 | B1 | | 9/2002 | Coates et al. | .......... 250/339.09 |
| 6,455,850 | B1 | | 9/2002 | Coates et al. | ............ 250/338.1 |
| 6,518,069 | B1 | | 2/2003 | Otvos et al. | |
| 6,576,471 | B2 | | 6/2003 | Otvos | |
| 6,617,167 | B2 | | 9/2003 | Otvos et al. | |
| 6,721,583 | B1 | * | 4/2004 | Durkin et al. | ............... 600/318 |
| 6,898,537 | B1 | * | 5/2005 | McGahan | ..................... 702/76 |

OTHER PUBLICATIONS

Kuller et al., *Nuclear Magnetic Resonance Spectroscopy of Lipoproteins and Risk of Coronary Heart Disease in the Cardiovascular Health Study*, Arteriosclerosis, Thrombosis, and Vascular Biology, vol. 22, No. 7, pp. 1175-1180, Jul. 2002.
Otvos, James, *What Lipids Don't Tell Us About Lipoproteins and Cardiovascular Disease Risk*, LVDD 15 Year Anniversary Issue, vol. XVI, No. 3, pp. 4, 14-18, Summer 2002.
Rosenson et al., *Relations of lipoprotein Subclass Levels and low-Density Lipoprotein Size to Progression of Coronory arter Disease in the Pravastatin Limitation of Atherosclerosis in the Coronary Arteries (PLAC-I) Trial*, The American journal of Cardiology, pp. 89-94, Jul. 15, 2002.
Hildebrand, F.B., *Introduction to Numerical analysis*, 2nd Edition, pp. 314-326, 539-567, McGraw-Hill, 1975.
International Search Report for International patent application No. PCT/US2003/33434 mailed on Dec. 21, 2005.

* cited by examiner

*Primary Examiner*—Marc S. Hoff
*Assistant Examiner*—Mary Catherine Baran
(74) *Attorney, Agent, or Firm*—Myers Bigel Sibley & Sajovec PA

(57) ABSTRACT

Methods, systems and computer programs are configured to determine the presence of and/or a measurement for a plurality of constituents in a composite signal with closely correlated chemical constituents having overlapping signal lineshapes extending about a spectrum of interest obtained from a target sample undergoing analysis.

45 Claims, 8 Drawing Sheets

METHODS, SYSTEMS AND COMPUTER PROGRAMS FOR DECONVOLVING THE SPECTRAL CONTRIBUTION OF CHEMICAL CONSTITUENTS WITH OVERLAPPING SIGNALS

RELATED APPLICATION

This application claims priority to U.S. Provisional Application Ser. No. 60/421,177, filed Oct. 25, 2002, the contents of which are hereby incorporated by reference as if recited in full herein.

FIELD OF THE INVENTION

The present invention relates generally to analysis methods of samples that produce signals with constituents having overlapping signals. The invention may be particularly suitable for NMR analysis of signals associated with biosamples, such as signals of lipoprotein constituents in blood plasma and serum.

BACKGROUND OF THE INVENTION

In the past, several analysis methods have been used to evaluate target materials, such as biosamples, that can generate a plurality of signals, each associated with a respective individual constituent in a complex mixture comprising a plurality of constituents, some of which may have overlapping signal contributions. The overlapping signals can produce a composite spectrum that can be deconvolved to estimate or determine the amount and/or presence of selected individual or subsets of constituents in the complex mixture. Such analysis methods include, but are not limited to spectroscopy, chromatography, and the like.

In the past, NMR spectroscopic evaluations of in vitro biosamples have been used to identify the presence of and/or measure the concentration or amounts of selected constituents in a complex mixture, the constituents having associated chemical lineshapes and/or peaks in the obtained NMR signal. For example, U.S. Pat. No. 4,933,844, entitled Measurement of Blood Lipoprotein Constituents by Analysis of Data Acquired from an NMR Spectrometer to Otvos and U.S. Pat. No. 5,343,389, entitled Method and Apparatus for Measuring Classes and Subclasses of Lipoproteins, also to Otvos, describe NMR evaluation techniques that concurrently obtain and then measure a plurality of different lipoprotein constituents in an in vitro blood or plasma sample. See also, U.S. patent application Ser. No. 10/208,371, entitled Method Of Determining Presence And Concentration Of Lipoprotein X In Blood Plasma And Serum, the contents of the above patents and patent application are hereby incorporated by reference as if recited in full herein.

Generally described, to evaluate the lipoproteins in a blood plasma and/or serum sample, the amplitudes and/or lineshapes of a plurality of NMR spectroscopy derived signals within a chemical shift region of the NMR spectrum are deconvoluted from the composite signal or spectrum, each signal component so deconvolved being associated with respective lipoprotein subclass constituents of interest or selected related groupings of subclass constituents of interest in the sample. The values of at least one selected subclass constituent (or groupings of selected subclass constituents) are compared to predetermined test criteria to evaluate a patient's risk of having or developing coronary artery or heart disease. Similarly, NMR spectroscopy evaluation of lipoproteins have been proposed to evaluate a patient's risk of having or developing insulin resistance, Type-2 diabetes, or related disorders. See, U.S. patent application Ser. No. 09/550,359, entitled Methods and Computer Program Products for Determining Risk of Developing Type 2 Diabetes and Other Insulin Resistance Related Disorders, the contents of which are hereby incorporated by reference as if recited in full herein.

Referring to FIG. 1, it is noted that the constituents of certain subclasses of lipoproteins have overlapping signals. For example, low-density lipoprotein ("LDL") constituent values, shown for clarity as only two (L2 and L5) LDL subclass constituent values, when presented on a spectrum graph of signal intensity versus ppm, can overlap considerably. The overlapping nature of the signals produces a regression matrix that is nearly singular. Unfortunately, in conventional statistical evaluation methods that can employ non-negative least squares techniques on nearly collinear data, the regression coefficients may be unstable and, hence, variable. See Myers, Raymond H., *Classical and Modern Regression with Applications,* (2d ed., Mass. PWS-Kent, 1990); Box et al., *Statistics for Experimenters; An Introduction to Design, Data Analysis, and Model Building,* (New York, Wiley, 1978). The potential instability in the regression coefficients can force the non-negative least squares analysis to set certain constituent coefficients to zero, although these constituents may be more correctly identified as small positive values when analyzed properly. Further, although conventional methods are thought to be adequate for many clinical or other applications, particularly in light of the margin of error introduced by other testing methodologies, the instability may impede the statistical robustness or reproducibility of certain measurement results.

In view of the foregoing, there remains a need to provide improved deconvolution methods.

SUMMARY OF EMBODIMENTS OF THE INVENTION

Certain embodiments of the present invention are directed at providing methods, systems, and computer program products that include operations that can provide increased robustness or stability in the fitting models, regression analysis protocols, and/or reproducibility in the measurements or evaluation of signals having spectral contribution from chemical constituents having overlapping signals.

The inventive methods, systems and computer program products may be able to interrogate the signal data of selected constituents in a composite spectrum signal of an unknown sample to identify the spectra or portion of the composite spectrum that is attributed to noise or non-relevant constituents or contributors rather than selected constituents of interest and thereby selectively discount or disregard the noise or constituents of non-relevance from the analysis. A constituent may be non-relevant if it is not a target of the analysis and, hence, not of primary or major interest in the end computation or output; however, the non-relevant constituent can contribute to the signal in a region of interest in the obtained composite data spectrum. Thus, in certain embodiments, operations contemplated by the present invention can consider the influence of these non-relevant contributors in the analysis to more properly assess or estimate the "true" values of the relevant constituents that increase the accuracy and/or reproducibility of the estimate of the relevant or target constituents of interest.

The evaluation may be particularly suitable for composite signals having at least about 10 individual constituents with highly or closely correlated signals. In certain embodiments, the evaluation can be performed on samples that have between 30-45, typically at least about 37 individual constituents. In certain embodiments, operations are carried out to generate the weighting coefficients without relying on negative values in the least squares solution set. Thus, the operations may decrease the number of constituents in the composite that have coefficients that are set to zero (previously associated with constituents identified as having negative signal values).

In certain embodiments, the operations can be carried out to more reliably measure discrete spectra contributions of chemical constituents with improved signal resolution without suppressing data for constituents of interest that previously may have been identified as having negative values. The evaluation can allow for improved resolution in assessing constituent values when deconvolving a complex mixture of constituents to measure or identify selected constituents within a composite spectrum having signal contributions associated with spatially overlapping individual constituent signals.

Methods for determining the presence of and/or a measurement for a plurality of constituents in a composite signal extending about a spectrum of interest obtained from a target sample undergoing analysis include: (a) generating a mathematical design matrix of constituent data comprising a plurality of selected individual mathematical constituent matrix data sets, each constituent matrix data set including constituent amplitude values of a respective spectrum lineshape of a selected independent parameter over a desired number of data points of a known reference sample that is generated by a predetermined analysis method; (b) generating a composite mathematical matrix comprising a data set of amplitude values of a composite spectrum lineshape of the selected independent parameter over the desired number of data points for a target sample undergoing analysis that is generated by the predetermined analysis method, the composite lineshape comprising spectral contributions from a plurality of the selected individual constituents included in the design matrix; (c) rotating the design matrix to provide a rotated design matrix of principal components; (d) selectively excluding data corresponding to certain of the principal components in the rotated design matrix; (e) generating a reduced design matrix based on the steps of rotating and excluding; and (f) computing regression fit weighting coefficients based on data in the reduced design matrix and the composite matrix for the plurality of individual constituents to determine the presence of and/or measurement of the selected constituents in the target sample.

The computing step can also employ a sequential regression to ensure non-negativity of the weighting coefficients. Stated differently, the computing step can include a sequential least squares restraint in a statistical regression analysis to force the defined weighting coefficients of target constituents of interest to be positive.

The constituent matrix can include at least 10 different data sets, each representing a respective one of at least 10 different closely correlated chemical constituents such that a plurality of the constituents have overlapping signal lineshapes in a region of the spectrum analyzed.

In certain embodiments, the predetermined analysis method is NMR spectroscopy and the composite and reference constituent signals represent intensity over a desired interval or region in a chemical shift spectrum such that intensity is the independent variable parameter.

The signals (sample and reference) may be spectrally aligned to a reference signal. For example, for NMR analysis of plasma samples, the signal can be referenced to the sharp NMR resonance peak produced by the calcium complex of EDTA that is present in the sample. The sample spectrum and the reference spectra can be shifted as needed to align the CaEDTA peak at 2.519 ppm on the horizontal scale. In addition, in certain embodiments, operations of the present invention can be carried out using alternative internal references used for signal alignment. For example, glucose or lactate signals or other desired constituent references can be used for spectral alignment purposes.

Other aspects of the invention are directed to computer program products for deconvolving the spectral contribution of a plurality of closely correlated constituents in a composite signal. The computer program product includes a computer readable storage medium having computer readable program code embodied in the medium. The computer-readable program code includes: (a) computer readable program code that generates a design matrix of individual selected constituent data sets for a plurality of different selected constituents in a spectrum of interest, each individual selected constituent data set including amplitude values of its associated spectral lineshape, wherein a plurality of the different selected constituents are closely correlated with overlapping signal lineshapes in the spectrum of interest; (b) computer readable program code that obtains a composite signal of a target sample undergoing analysis and generates a composite matrix of amplitude values of the lineshape of the composite signal in the spectrum of interest, the target sample comprising spectra from a plurality of the selected closely correlated constituents that contribute to the composite signal; (c) computer readable program code for rotating the design matrix; (d) computer readable program code that generates a reduced design matrix; and (e) computer readable program code that computes regression fit weighting coefficients based on the design matrix, the reduced matrix, and the composite matrix to thereby deconvolve the spectral contribution of at least one non-target variable across the spectrum of interest in the composite signal.

Still other aspects of the present invention are directed toward methods of deconvolving a complex signal to evaluate an in vitro biosample. The methods include: (a) obtaining a plurality of individual NMR spectrum reference signals of selected target constituents of interest in an in vitro biosample; (b) obtaining a composite NMR spectrum signal of the in vitro biosample taken from a subject for analysis, the composite signal including spectral contributions from a plurality of the individual target constituents of interest; (c) generating a design matrix of individual data sets of the amplitude of the respective reference constituents in the NMR spectrum, the design matrix having columns or rows of data that correspond to principal components that contribute to the spectral lineshape of the composite signal; (d) rotating the design matrix; (e) generating a reduced design matrix of principal component data by selectively excluding principal components that do not improve the estimation of the target constituents in the composite signal; (f) deriving regression fit weighting coefficients for the selected target constituents in the composite signal; (g) generating a calculated composite lineshape for the sample, the calculated lineshape being calculated based on the derived weighting coefficients of respective constituent reference spectrums of constituents potentially present in the sample, and (h) determining the presence or absence of and/or the level or concentration of at least one selected constituent in the sample.

Additional aspects of the present invention include apparatus for measuring lipoprotein constituents in a subject. The apparatus includes: (a) an NMR spectrometer for acquiring an NMR composite spectrum of a blood plasma or serum sample; (b) computer program code defining a plurality of individual NMR constituent spectrums, each associated with a selected reference lipoprotein constituent signal lineshape, each constituent spectrum having associated spectra that contribute to the composite NMR spectrum of the blood plasma or serum sample; (c) computer program means for generating a design matrix of the selected individual constituents, the design matrix including data sets for each of the plurality of individual lipoprotein constituents in a spectrum of interest, each individual selected constituent data set including amplitude values of its associated spectral lineshape, wherein a plurality of the selected individual constituents are closely correlated with overlapping signal lineshapes in the spectrum of interest; (d) computer program means that obtains a composite signal of a target sample undergoing analysis and generates a composite matrix of amplitude values of the lineshape of the composite signal in the spectrum of interest, the target sample comprising spectra from a plurality of the selected individual constituents that contribute to the composite signal; (e) computer program means for rotating the design matrix; (f) computer program means for generating a reduced design matrix; (g) computer program means for computing regression fit weighting coefficients based on the design matrix, the reduced matrix, and the composite matrix to deconvolve the spectral contribution of at least one non-target variable across the spectrum of interest in the composite signal; (h) computer program means for applying a sequential least squares analysis to the regression fit weighting coefficients to restrain negative coefficients to zero; (i) computer program means for determining a calculated composite lineshape based on the weighting coefficients; and (j) computer program means for determining the concentrations of the lipoprotein constituents in the sample undergoing analysis.

Other aspects include apparatus for determining the presence of and/or a measurement for a plurality of constituents in a composite signal extending about a spectrum of interest obtained from a target sample undergoing analysis. The apparatus includes: (a) means or generating a mathematical design matrix of constituent data comprising a plurality of selected individual mathematical constituent matrix data sets, each constituent matrix data set including constituent amplitude values of a respective spectrum lineshape of a selected independent parameter over a desired number of data points of a known reference sample that is generated by a predetermined analysis method; (b) means for generating a composite mathematical matrix comprising a data set of amplitude values of a composite spectrum lineshape of the selected independent parameter over the desired number of data points for a target sample undergoing analysis that is generated by the predetermined analysis method, the composite lineshape comprising spectral contributions from a plurality of the selected individual constituents included in the design matrix; (c) means for rotating the design matrix to provide a rotated design matrix of principal components; (d) means for selectively excluding data corresponding to certain of the principal components in the rotated design matrix; (e) means for generating a reduced design matrix based on the steps of rotating and excluding; and (f) means for computing regression fit weighting coefficients based on data in the reduced design matrix and the composite matrix for the plurality of individual constituents to determine the presence of and/or measurement of the selected constituents in the target sample.

As will be appreciated by those of skill in the art in light of the present disclosure, embodiments of the present invention may include methods, systems, apparatus and/or computer program products or combinations thereof.

The foregoing and other objects and aspects of the present invention are explained in detail in the specification set forth below.

DETAILED DESCRIPTION OF EMBODIMENTS OF THE INVENTION

Figure 1:
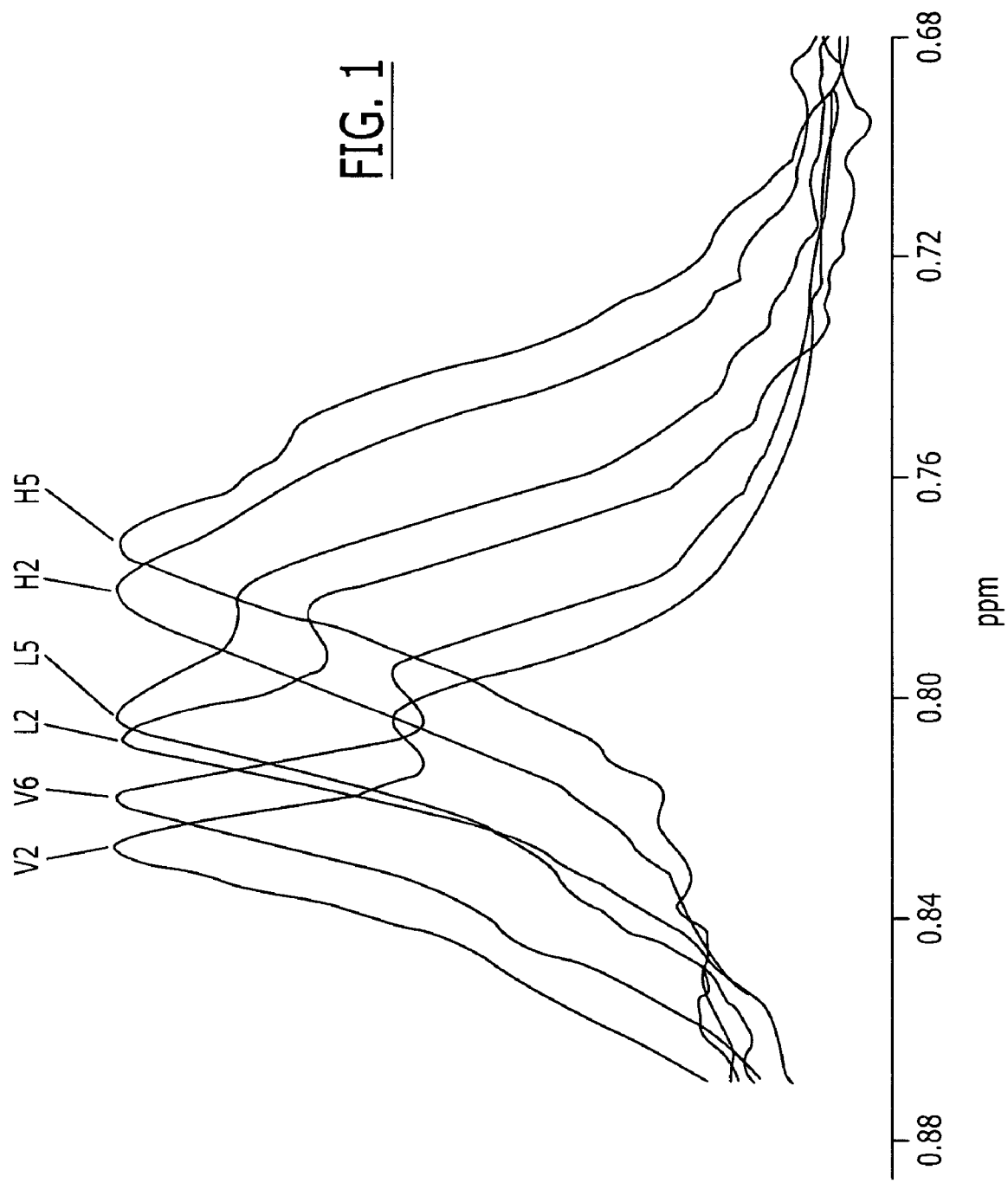
FIG. 1 is a graph showing the chemical shift spectra of a representative sample of lipoprotein constituent subclasses.

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout, and thickness, size and dimensions of some components, lines, or features may be exaggerated for clarity. The order of operations and/or steps illustrated in the figures or recited in the claims are not intended to be limited to the order presented unless stated otherwise. The broken lines in the figures indicate that the feature or step so indicated is optional.

In certain embodiments, the methods, systems, and/or computer products provided by the present invention employ statistical fitting models which evaluate signal data of an unknown sample according to a predetermined fitting model and standards to identify the presence of at least one selected chemical constituent and/or to measure the level or concentration thereof in the sample. More typically, the models, programs, and methods of the present invention are configured to evaluate signal data of a composite sample with highly or closely correlated individual constituent spectra (having at least a plurality with overlapping signal lines in the spectrum) to identify the presence of at least 10 different individual constituents and/or the level thereof. The term "highly" and "closely" are used interchangeably when used with "correlated" so that in the description that follows either "highly correlated" or "closely correlated" means that a plurality of constituents in a sample being analyzed generate respective spectra which can overlap in a composite signal that includes spectral contributions from those constituents.

Although described herein primarily with respect to NMR-derived spectroscopic signal evaluation of blood and/or plasma samples to determine lipoprotein values (such as particle size and/or concentrations), the present invention is not limited thereto. The operations of the present invention may be used to evaluate any suitable target sample, such as engineered, fabricated or forensic materials undergoing material science, quality inspection, forensic or other evaluations, as well as environmental samples, or other types of biosamples. Examples of additional biosamples include, but are not limited to, biopsy tissue samples, biofluid samples, stool samples, and the like. In addition, the present invention is not intended to be limited to NMR spectroscopy signals, as other analysis techniques are contemplated by the present invention. It is contemplated that operations of the present invention can find application in other spectroscopic analysis, chromatography, SEM (scanning electron microscope) evaluation, optical signal evaluation, gel electrophoresis, and any other analysis techniques that can benefit from deconvolving the spectral contribution of several chemical, optical (fluorescence, radiation, transmittance, reflectance and the like), or other measurable constituents having overlapping signals or spectral contribution in a composite signal.

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java®, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

A. General Description of NMR Spectroscopy of Lipoproteins in Blood and Plasma $^1$H NMR spectra of human blood plasma contain two prominent peaks centered at approximately 1.2 and 0.8 ppm (relative to the chemical shift standard, TSP). These peaks arise from methylene ($CH_2$) and methyl ($CH_3$) protons, respectively, of plasma lipids. Each of these peaks is very heterogeneous in nature, consisting of overlapping resonances from protons of the several chemically distinct classes of lipids present in plasma: triglycerides; cholesterol; cholesterol esters; and phospholipids. These lipids are packaged together into three major classes of lipoprotein particles, which differ in the proportions of lipids which they contain. These lipoprotein particles also differ in density from which their names are derived: very low density lipoprotein (VLDL), low density lipoprotein (LDL), and high density lipoprotein (HDL).

These major classes of lipoprotein constituents may be further subdivided into subclasses. A subclass of lipoprotein particles comprises constituents that have common physical properties, such as density, which permit a subclass to be fractionated from other subclasses and that exhibits NMR properties that are distinct from other subclasses. The NMR properties of one subclass may be distinct in a number of ways, such as chemical shift or lineshape variations, which make the subclass distinguishable from other subclasses. Subclasses distinguished upon density may be considered as a subclass of the class of lipoprotein that contains particles of the subclasses density. Delination of lipoprotein subclasses is discussed in U.S. Pat. No. 5,343,389 to Otvos, the disclosure of which was incorporated above in its entirety as if recited herein.

Lipoprotein subclass information is not included in conventional commercially prepared lipid panels. The conventional panels typically only provide information concerning total cholesterol, triglycerides, low-density lipoprotein (LDL) cholesterol (generally a calculated value), and high-density lipoprotein (HDL) cholesterol. In contrast, the NMR lipoprotein subclass analysis can provide information about (a) the concentrations of a plurality of individual or groupings of similar subclasses of: selected ones or groupings of at least about six very low density lipoprotein (VLDL) (V1-V6), selected ones or groupings of at least about four subclasses of LDL (including intermediate-density IDL) (L1-L4), and selected ones or groupings of at least about five subclasses of HDL (H1-H5), (b) average LDL particle size (which can be used to categorize individuals into LDL subclass pattern-determined risk such as Pattern A, AB, or B), and (c) LDL particle concentration (elevated concentrations being associated with increased cardiovascular risk). The phrase "selected ones or groupings" of subclass constituents means that each individual subclass constituent can be measured or that combined related subclasses may be used to provide the constituent subclass measurement. For example, V1 may include the constituents of V2 and/or V3, and V6 may be measured alone or may be measured as inclusive of V4 and/or V5. In other embodiments, V1, V2 and V3 could be independently assessed and separately reported. Similar individual assessments or groupings may be carried out for other related subclasses groupings of LDL (that may include IDL) and HDL. See U.S. patent application Ser. No. 09/992,068, entitled Methods, Systems, and Computer Program Products for Analyzing and Presenting NMR Lipoprotein-Based Risk Assessment Results, for further description of risks associated with measured values of subclasses, the contents of which are hereby incorporated by reference as if recited in full herein.

Generally described, only the fraction of the lipids in these lipoprotein particles that are in a fluid, mobile state (as opposed to an ordered liquid-crystalline state) contribute to the plasma lipid NMR resonances. The heterogeneity of these plasma signals is reflected by their complex lineshapes, which vary from person to person owing to variations of the plasma concentrations of the different lipoprotein particles, each of which has its own characteristically different NMR spectral properties.

NMR spectroscopy can be employed to determine the concentrations of lipoprotein classes (VLDL, LDL, HDL, and chylomicrons) and lipoprotein subclasses of a blood and/or plasma sample, as well as a protein constituent, by a computer analysis of the lineshapes of its methyl and methylene signals (use of the methyl signal alone has been found to be preferable). This region of the observed plasma spectrum can be accurately represented by a simple linear combination of the spectra of the major lipoprotein and protein classes and/or subclasses noted above into which plasma can be fractionated by differential flotation ultracentrifugation.

The NMR spectral properties of these classes have been found to be quite similar from person to person. Thus, differences among the NMR signals that form the plasma of individuals are caused by differences in the amplitudes of the lipid resonances for these constituents, which in turn are proportional to their concentrations in the plasma.

Figure 2:
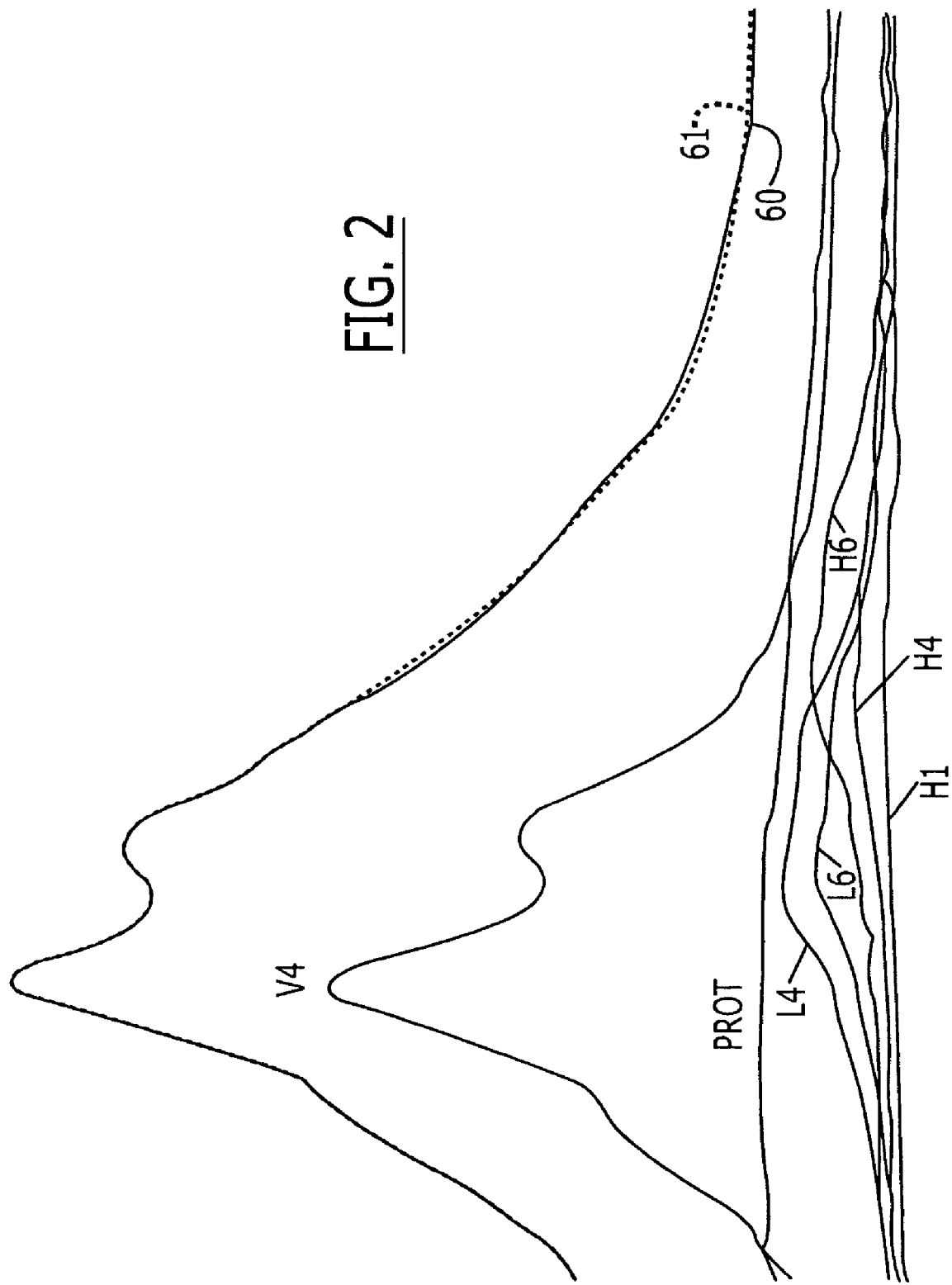
FIG. 2 is a graph illustrating NMR spectra for a plasma sample and the lipoprotein subclass and protein components thereof, with the peaks for methyl groups being illustrated.

The small person-to-person variations in the lineshapes of the lipoprotein classes are caused by the subclass heterogeneity known to exist within each of these lipoprotein classes. FIG. 1 shows the lineshapes and chemical shifts (positions) for a number of subclasses of lipoproteins. As shown in FIG. 1, the chemical shifts and lineshape differences between the subclasses are much smaller than those between the major lipoprotein classes, but are completely reproducible. Thus, differences among the NMR signals from the plasma of individuals are caused by differences in the amplitudes of the lipid resonances from the subclasses present in the plasma, which in turn are proportional to their concentrations in the plasma. This is illustrated in FIG. 2, in which the NMR chemical shift spectra of a blood plasma sample is shown. The spectral peak produced by methyl ($CH_3$) protons 60 (shown as a solid line) is shown for the blood sample in FIGS. 2. The spectral peak 61 (shown as a dotted line) in FIG. 2 is produced by the arithmetic sum of the NMR signals produced by the lipoprotein subclasses of the major classes VLDL, LDL, HDL, proteins and chylomicrons, as illustratively shown by certain of the subclasses in FIG. 1. It can be seen that the lineshape of the whole plasma spectrum is dependent on the relative amounts of the lipoprotein subclasses whose amplitudes change (sometimes dramatically) with their relative concentrations in the plasma sample.

Since the observed $CH_3$ lineshapes of whole plasma samples are closely simulated by the appropriately weighted sum of lipid signals of its constituent lipoprotein classes, it is possible to extract the concentrations of these constituents present in any sample. This is accomplished by calculating the weighting factors which give the best fit between observed blood plasma NMR spectra and the calculated blood plasma spectra. Generally speaking, the process of NMR lipoprotein analysis can be carried out by the following steps: (1) acquisition of an NMR "reference" spectrum for each of the "pure" individual or related groupings of constituent lipoprotein classes and/or subclasses of plasma of interest, (2) acquisition of a whole plasma NMR spectrum for a sample using measurement conditions substantially identical to those used to obtain the reference spectra, and (3) computer deconvolution of the plasma NMR spectrum in terms of the constituent classes and/or subclasses (or related groupings thereof) to give the concentration of each lipoprotein constituent expressed as a multiple of the concentration of the corresponding lipoprotein reference.

In the past, the plasma lineshape analysis was accomplished by calculating weighting coefficients for each of the reference NMR spectra which minimize the sum of squared deviations and iteratively removing those constituents having negative values between the observed plasma NMR spectrum and that which is calculated by summing the weighted reference spectra. Typically, a correlation coefficient (calculated by the method described below) between the measured spectrum and the calculated lineshape of at least 0.999 was used to indicate a successful deconvolution of the spectrum.

Although, as inferred above, the procedure can be carried out on lipoprotein classes, carrying out the process for subclasses of lipoproteins can decrease the error between the calculated lineshape and the NMR lineshape, thus increasing the accuracy of the measurement while allowing for simultaneous determination of the subclass profile of each class. Because the differences in subclass lineshapes and chemical shifts are small, it is typically important to correctly align the reference spectrum of each subclass with the plasma spectrum. The alignment of these spectra is accomplished by the alignment of control peaks in the spectra, which are known to respond in the same manner to environmental variables, such as temperature and sample composition, as do the lipoprotein spectra. One such suitable alignment peak is the peak produced by CaEDTA, although other EDTA peaks or suitable peak may be utilized. By alignment of the spectra, the small variations in the subclasses' lineshapes and chemical shifts may be exploited to produce higher accuracy and subclass profiles.

Further description of these methods can be found in U.S. Pat. Nos. 4,933,844 and 5,343,389 to Otvos.

B. Lineshape

The mathematics used in the lineshape fitting process (i.e., least squares fit of an unknown function in terms of a weighted sum of known functions) is well known and is described in many textbooks of numerical analysis, such as F. B. Hildebrand, *Introduction to Numerical Analysis,* 2nd edition, pp. 314-326, 539-567, McGraw-Hill, 1975.

Figure 6:
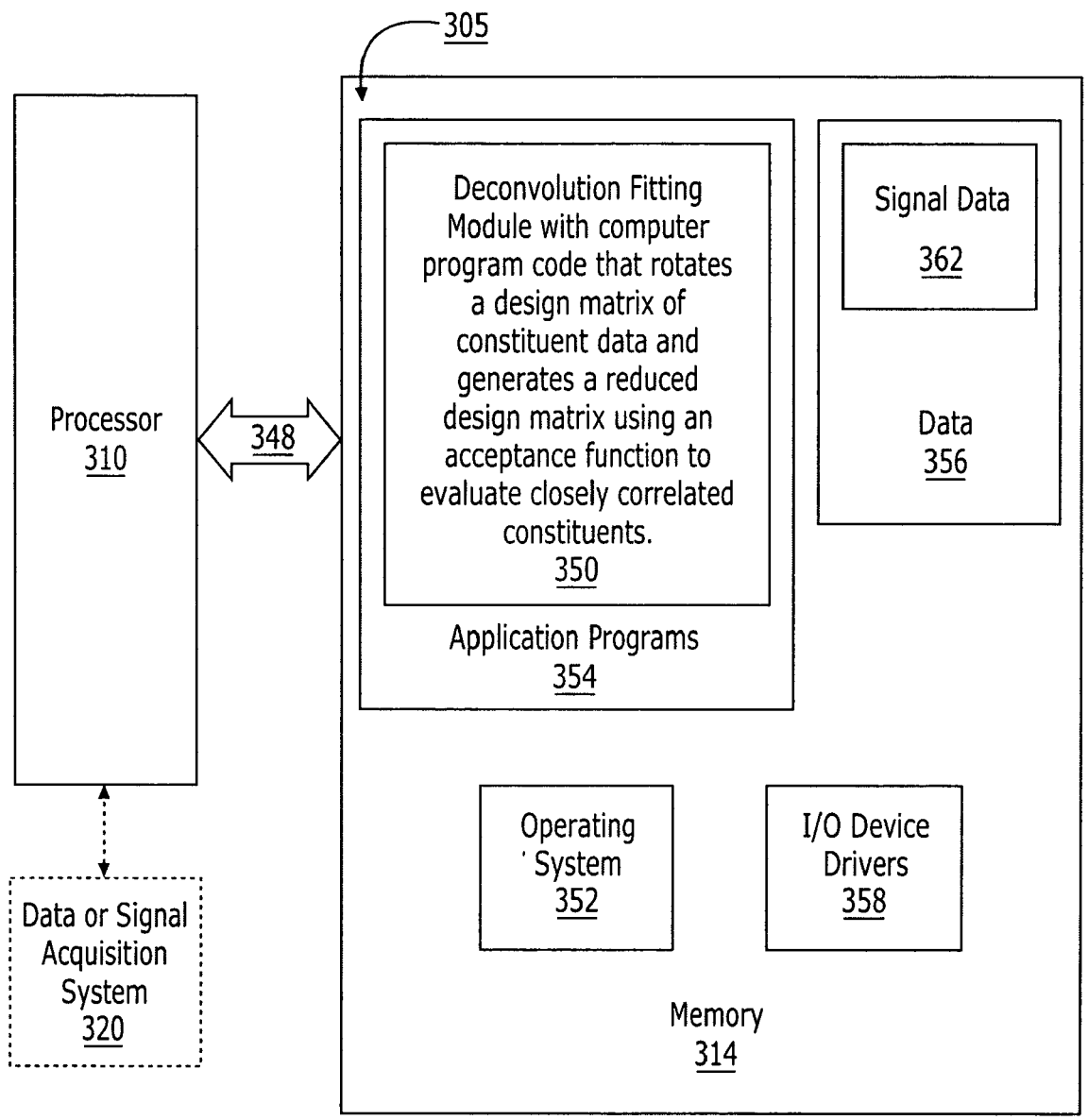
FIG. 6 is a schematic diagram of a data processing system according to embodiments of the present invention.
Figure 7:
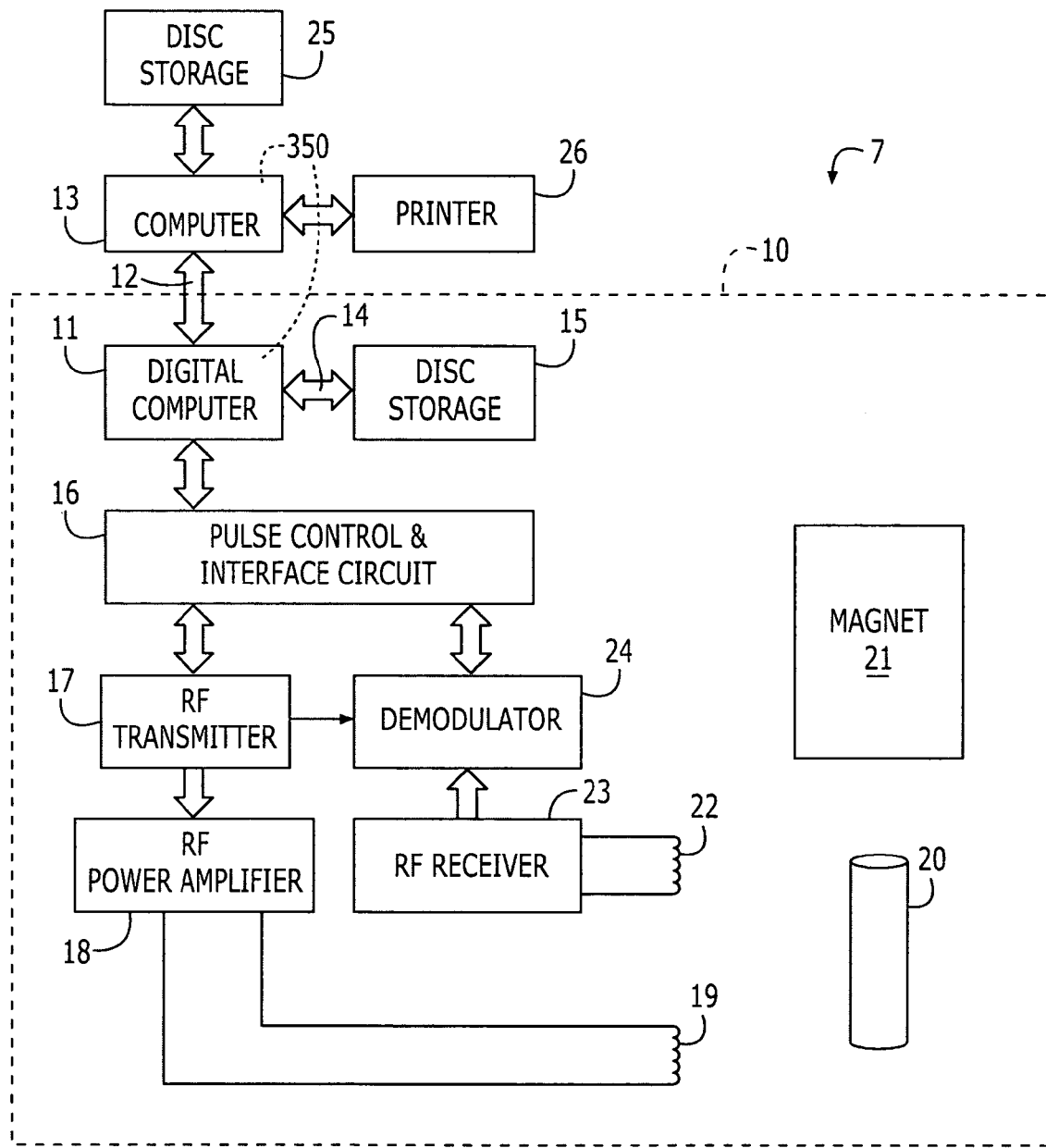
FIG. 7 is a schematic diagram of an apparatus for measuring lipoprotein concentrations of a blood or plasma sample according to embodiments of the present invention.

In particular embodiments, reference samples of each constituent lipoprotein and protein component to be analyzed are prepared (typically they are refrigerated during storage and allowed to warm prior to analysis) and placed within the spectrometer 10 (FIG. 7). An NMR measurement is then taken on each reference sample to define a standard for the respective constituent. The data for the reference samples (for a plurality of different constituents) is processed and stored in a processor 310 (FIG. 6) and/or computer (such as shown for feature 11 in FIG. 7). Techniques for acquiring and storing NMR spectroscopic data are well-known to those skilled in this art and need not be described in further detail. The reference samples or standards may be established a priori and used to measure a plurality of different patient specimens or samples over time.

To carry out the analysis, the data points of the real part of the sample plasma spectrum that comprise the spectral region to be fit (normally 0.73-0.85 ppm for lipoprotein evaluations) are entered into an array. This plasma array consists of m discrete data points denoted $P_i^o$, i=1, 2, ... m. The data points of the real part of the lipoprotein subspecies reference spectra for the same spectral region are entered into separate arrays. The data points of these arrays are denoted $V_{ji}$, where i=1, 2, ... m data points and j=1, 2, ... n constituents). It is noted that in the Equations and text describing same that follows, some symbols may be bolded and/or italicized at certain locations but not at other locations, however this is not meant to alter the correlation or change the meaning of the symbol herein.

The method for fitting the measured sample plasma spectrum, $P_i^o$, with a linear combination of n constituent spectra is based on the premise that there are a set of coefficients (weighting factors), $c_j$, corresponding to the contributions of components (lipoprotein subclass components and protein component), and a coefficient, $c_p^1$ corresponding to the imaginary portion of the sample plasma spectrum, such that for each data point, $P_i^o \approx P_i^c$, where $$P_i^c = \left(\sum_{j=1}^{n} c_j V_{ji}\right) + c_p^I V_i^I \text{(calculated plasma spectrum)}. \quad (1)$$

In the past, the best fit was achieved when the root mean square error, $$\sqrt{\frac{1}{m-n}(\sum \epsilon_i^2)} \quad (2)$$

was minimized, where $\epsilon = P_i^o - P_i^c$. This was accomplished by finding those coefficients which minimize $\Sigma \epsilon_i^2$, that is, when $$\frac{\partial \sum \epsilon_i^2}{\partial c_j} = 0, \quad (3)$$

j=1, 2, ... n+1 (n−1 subspecies components plus protein and plasma spectrum phase contributions). Differentiation results in n+1 simultaneous linear equations:

$$\sum_{i=1}^{m} P_i^o V_{ki} = \sum_{j=1}^{n+1} c_j \left(\sum_{j=1}^{M} V_{ki} V_{ji}\right), k = 1, 2, \ldots n+1 \quad (4)$$

If (5)

$$a_{kj} = \sum_{j=1}^{m} V_{ki} V_{ji} \text{ and } s_k = \sum_{i=1}^{m} P_i^0 V_{ki}$$

then there are n+1 simultaneous linear equations of the form:

$$\sum_{j=1}^{m} c_j a_{kj} = s_k, k = 1, 2, \ldots n+1 \quad (6)$$

Forming the n+1×n+1 matrix, [A]=[$a_{kj}$], j=1, 2 ... n+1; k=1, 2 ... n+1, gives [A]C=S, where C and S are the column vectors, $$\begin{bmatrix} c_1 \\ c_2 \\ \vdots \\ c_n \\ c_{n+1} \end{bmatrix} \text{ and } \begin{bmatrix} s_1 \\ s_2 \\ \vdots \\ s_n \\ s_{n+1} \end{bmatrix} \quad (7)$$

The coefficients providing the best fit were calculated by decomposition of the matrix [A] into a new set of m×m matrices known collectively as the "singular value decomposition" of [A]:

$$[A]=[U][W][V]^T \quad (8)$$

where [U] is a matrix of orthogonal column vectors (scalar products=0), [V]$^T$ is the transpose of an orthogonal matrix [V], and [W] is a diagonal matrix with positive or zero elements, called "singular values:"

$$[W] = \begin{bmatrix} w_1 & 0 & \cdots & 0 \\ 0 & w_2 & \cdots & 0 \\ \vdots & \vdots & \ddots & \vdots \\ 0 & 0 & \cdots & w_m \end{bmatrix} \quad (9)$$

From this, $$[A]^{-1}=[V][W]^{-1}[U]^T \quad (10)$$

$$\text{where } [W]^{-1} = \begin{bmatrix} 1/w_1 & 0 & \cdots & 0 \\ 0 & 1/w_2 & \cdots & 0 \\ \vdots & \vdots & \ddots & \vdots \\ 0 & 0 & \cdots & 1/w_m \end{bmatrix} \quad (11)$$

which allows C to be solved for:

$$C = [V][W]^{-1}[U]^T S \quad (12)$$

where C was the best possible solution vector, provided that values of $w_j$ below a certain threshold value (selected by the user) are ignored ($1/w_j$ set to zero). These singular values can give rise to "ill-conditioned" linear combinations of near degenerate solutions, being most corrupted by roundoff errors. The actual solution of C was obtained by "back-substitution" in which $w_m$ is determined, allowing for the solution of $w_{m-1}$, etc.

The root mean square deviation (RMSD) is computed as $$\sigma \text{RMS} = \sqrt{\frac{1}{m-n-1} \sum_{i=1}^{m} (P_i^o - P_i^c)^2} \quad (13)$$

The correlation coefficient was computed as $$r^P = \frac{\sum_{i=1}^{m} (P_i^o - \langle P_i^o \rangle)(P_i^c - \langle P_i^c \rangle)}{\sqrt{\left(\sum_{i=1}^{m} (P_i^o - \langle P_i^o \rangle)^2 \sum_{i=1}^{m} (P_i^c - \langle P_i^c \rangle)^2\right)}} \quad (14)$$

In the past, the component coefficients resulting from this lineshape analysis provided the concentrations of the lipoprotein and protein constituents in each plasma sample. Each concentration can be expressed relative to the concentration of the lipoprotein whose spectrum is used as the reference. In operation, the final concentrations may be normalized to the integrated area of the resonance from a tri-methylacetate external standard sample run on the same day to correct for variations in the detection sensitivity of the NMR spectrometer.

As described above, the least squares method used in the past for NMR-derived measurement of lipoprotein subclasses required that the derived concentrations be a positive value. Generally described, in the past, when a negative coefficient for a selected constituent associated with one of the standards was encountered it was constrained to zero, and the calculation was performed again, subject to that constraint. The latter constraint can be desirable when fitting plasma samples that may not contain one or more of the components included in the fit model or because experimental errors in the data (noise) can cause the calculation to give negative values for concentrations for these components.

Figure 3:
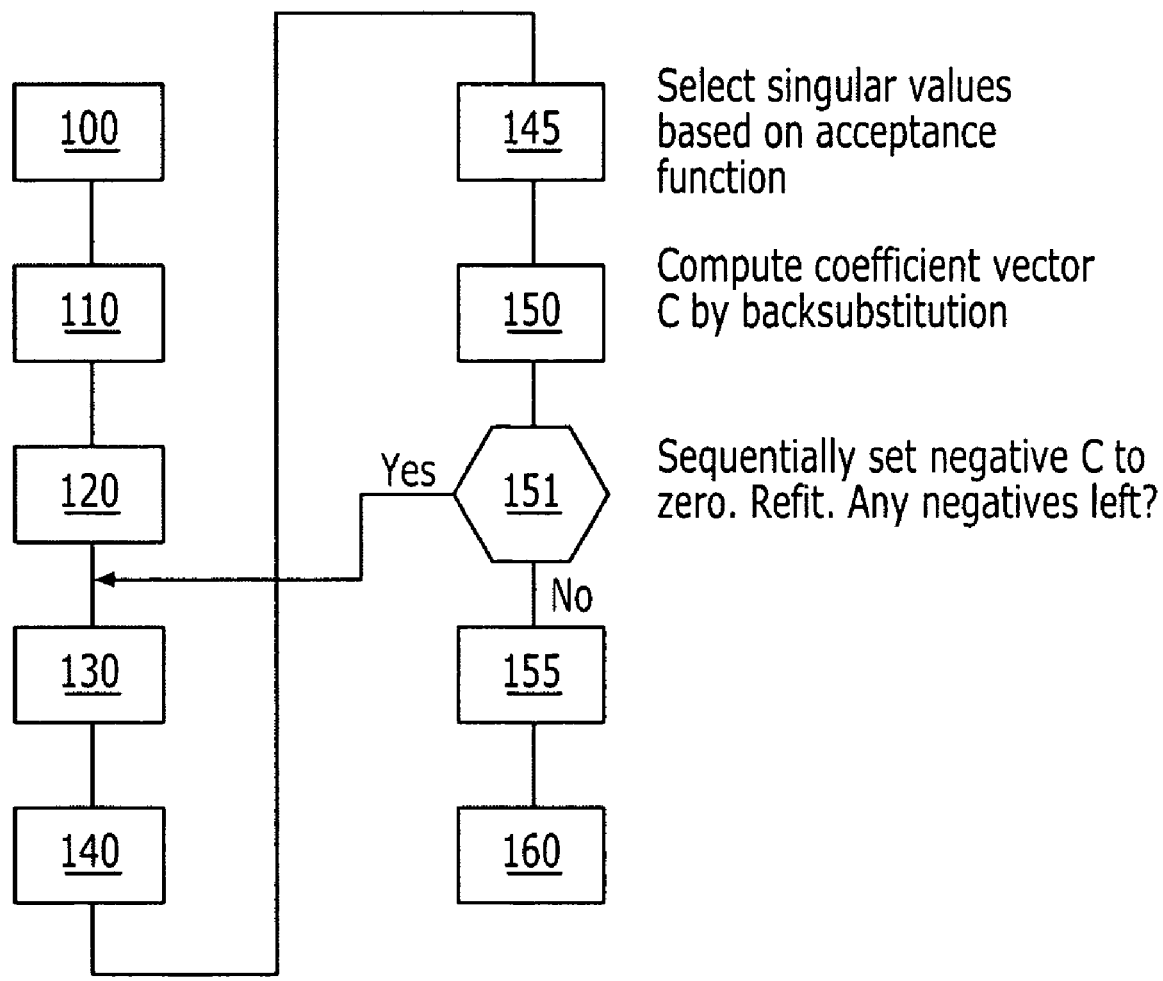
FIG. 3 is a block diagram of operations that can be used to evaluate signal data according to embodiments of the present invention.

FIG. 3 illustrates a flow chart of operations with reference to certain of the above-stated equations in blocks 100-160. In operation, spectra of subspecies components is read into Array V (block 100). The real part of the sample plasma spectrum is read into Array $P^o$ (block 110). The imaginary part of the sample plasma spectrum is read into the Array V (block 120). Marix [A] and S vector are calculated (block 130) using Equation 5. Matrix [A] is decomposed into a singular value decomposition (block 140) such as by using Equation 8. The singular values are selected based on a predetermined acceptance function (block 145). The coefficient vector C is calculated using back substitution (block 150). The negative values in C are sequentially set to zero and the curve is refit, until there are no negatives left. The yes or no inquiry at (block 151) asks whether there are negatives left and, if so, directs the program to return to the operation in (block 130) and if not, directs the operations to advance to (block 155). C is multiplied by normalization constants to obtain concentrations (block 155). The root mean square deviation and correlation coefficient are calculated (block 160) such as by using Equations 13 and 14.

Embodiments of the present invention modify and improve on the conventional protocol by employing operations that can reduce measurement variability in individual constituents and/or by reducing the number of constituents of interest that are reported as having a "0" value. The variability can be assessed by repeatedly analyzing a given sample and measuring the individual constituents. The individual constituents measured by the present invention will typically be clustered more tightly together relative to the individual constituents measured by the conventional protocol. The methods and systems of the present invention can reduce the variability by at least about 50% relative to the prior method for the same sample. Further, when analyzing the same sample in repeated interrogations, the measured values of at least a majority of the constituents of interest, if not all of the constituents of interest, can be reproducible, typically within about +/−2.34% (median CV). See Table 2 in the Example Section.

Figure 4:
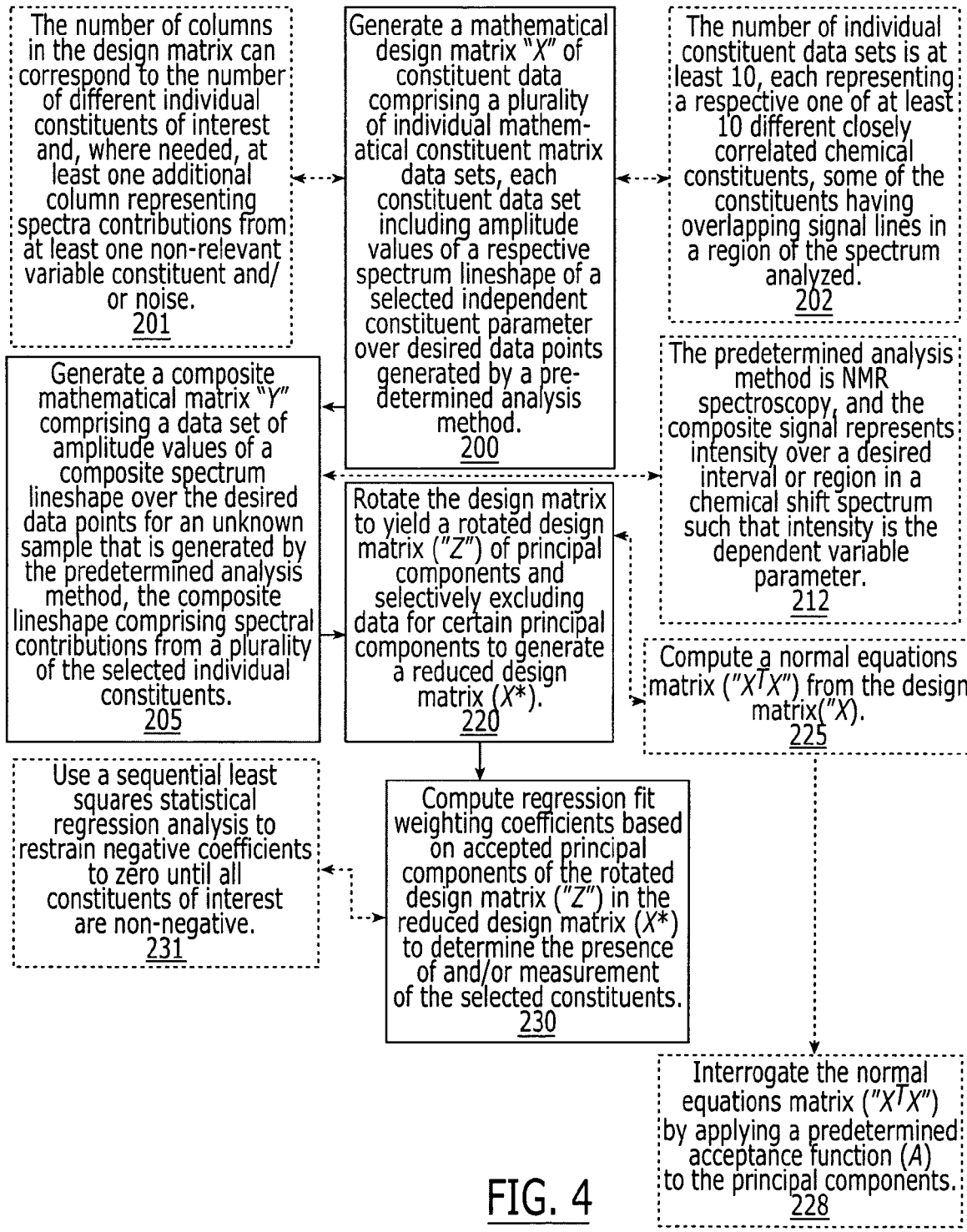
FIG. 4 is a block diagram of operations that can be used to evaluate signal data according to embodiments of the present invention.

Referring now to FIG. 4, operations of certain embodiments of the invention are illustrated. It is noted that the term "matrix," as used herein, can, in certain embodiments, be a vector, as a vector is a special form of a matrix (i.e., a vector is a matrix with n rows and 1 column, or 1 row and k columns). As shown in FIG. 4, the operations can include generating a mathematical design matrix of constituent data comprising a plurality of mathematical constituent matrix data sets, each constituent data set including amplitude values of a respective spectrum lineshape of a selected independent constituent parameter over desired data points generated by a predetermined analysis method (of a known reference sample) (block 200). The selected constituent parameter (the independent parameter) can be wavelength, voltage, current, speed, force, torque, pressure, movement, energy, chemical shift (ppm), temperature, frequency. Exemplary dependent parameters of interest may include, but are not limited to, intensity, opacity, transmittance, reflectance, fluorescence, vibration, or other desired parameter. The constituent data of the design matrix ("X") can be reference or standard data established a priori from separate individual analysis of discrete constituents of interest and/or stored in an accessible database to be used as a standard and applied in analysis of all or selected ones of unknown samples.

A composite mathematical matrix can be generated comprising a data set of amplitude values of a composite spectrum lineshape over the desired data points for an unknown sample that is generated by a predetermined analysis method. The composite lineshape comprises spectral contributions from a plurality of the selected individual constituents (block 205). The design matrix can be rotated to yield a rotated design matrix of principal components (which may, in certain embodiments, be mathematically represented by matrix "Z" as will be discussed further below) and processed to selectively exclude data for certain principal components to generate a reduced design matrix (which may, in certain embodiments, be represented mathematically by matrix "X*" as will be discussed further below) (block 220). The term "principal components" means individual identifiable constituents (and may include both relevant and non-relevant constituents) in the rotated space. In operation, in certain embodiments, the operations can include mathematically rotating the design matrix, interrogating the rotated design matrix (using an acceptance function) to find those rotated principal components with contributions that benefit the deconvolution, and rotating back those accepted principal components to form the reduced design matrix.

In certain embodiments, a normal equations matrix (which, in certain embodiments, may be mathematically represented by matrix "$X^T X$") can be computed from the design matrix (block 225). The normal equations matrix can be interrogated by applying a predetermined acceptance function ("$A(\lambda)$") to the principal components to generate the reduced design matrix. The acceptance function can be a forced logic function of "0" and "1" (representative of rejected (excluded) values and accepted (included) values, respectively) or may be a relative or absolute function that discards the principal components having values low with respect to other components or relative to a predefined threshold (i.e., the values having the least significance) and retaining the more significant values in the reduced design matrix. The reduced matrix may be generated by rotating the design matrix and eliminating the column or columns in the rotated design matrix with the most "0"s as determined by the acceptance function.

Regression fit weighting coefficients can be computed based on accepted principal components of the rotated design matrix in the reduced design matrix to determine the presence of and/or measurement of the selected or target constituents in the unknown sample undergoing analysis (block 230). In particular embodiments, the weighting coefficients may be determined according to Equation (20) as will be discussed further below. A sequential least squares regression analysis can then be employed to restrict or restrain negative coefficients to zero until all (or substantially all) constituents of interest are non-negative (block 231). In certain embodiments, before the sequential regression analysis evaluation is performed, the reduced design matrix is combined with the composite matrix to define a first set of weighting factors.

Described differently, the signal from the unknown test sample can be projected onto the space spanned by selected principal components and the projection coefficients can be transformed back into the original space to provide a reduced design matrix for arriving at weighting coefficients. As such, the design matrix can be mapped into the rotated design matrix and the components selected to yield the reduced design matrix.

The reduced design matrix can be generated based on predetermined criteria using a shrinkage estimator. In certain embodiments, the shrinkage estimator can be based on the spectral decomposition of a matrix defined by the multiplication of the constituent matrix with the transposed constituent matrix. In certain embodiments, the shrinkage estimator can be found by projecting the constituent matrix onto the space spanned by the accepted basis set determined from the rotation of the design matrix, and shrinking the projection of the constituent matrix on the orthogonal subspace to zero. A particularly suitable shrinkage estimator is described in Equation (20).

It is noted that other shrinkage estimators may also be employed. Generally stated, a shrinkage estimator of a parameter b is any estimator $B(X)$ of the data X such that $\|E\{B(X)\}\|<\|b\|$. A simple example would be to take an unbiased estimator of b, say $U(X)$, and multiply by a constant smaller than 1: $B(X)=pU(X)$ where $0<p<1$. Because $U(X)$ is unbiased, by definition of unbiased, $E\{U(X)\}=b$. Then the norm of the expectation could be expressed as $\|E\{B(X)\}\|=\|E\{p\ U(X)\}\|=p\|E\{U(X)\}\|=p\|b\|<\|b\|$ since $p<1$. In the shrinkage estimator of Equation (20), shrinkage is carried out selectively, in the direction of zero for some components, and not for others.

The number of individual constituent data sets can be at least ten (10), each representing a respective one of at least ten (10) different closely correlated chemical constituents, some of the constituents having overlapping signal lines in a region of the spectrum analyzed (block 202). The number of columns in the design constituent matrix can correspond to the number of different individual constituents of interest, and, where needed, at least one additional column, which may be a matrix of variables, representing spectra contributions from at least one non-relevant variable constituent and/or noise (block 201). In operation, this additional column may not be used (i.e., "0"). The at least one non-relevant variable can be a constituent known to be in the sample but not a target interest and/or background or environmental noise, and the like.

In certain embodiments, the predetermined analysis method is NMR spectroscopy, and the composite signal represents intensity over a desired interval or region in a chemical shift spectrum (typically represented in ppm) such that intensity is the dependent variable parameter (block 212).

Figure 5:
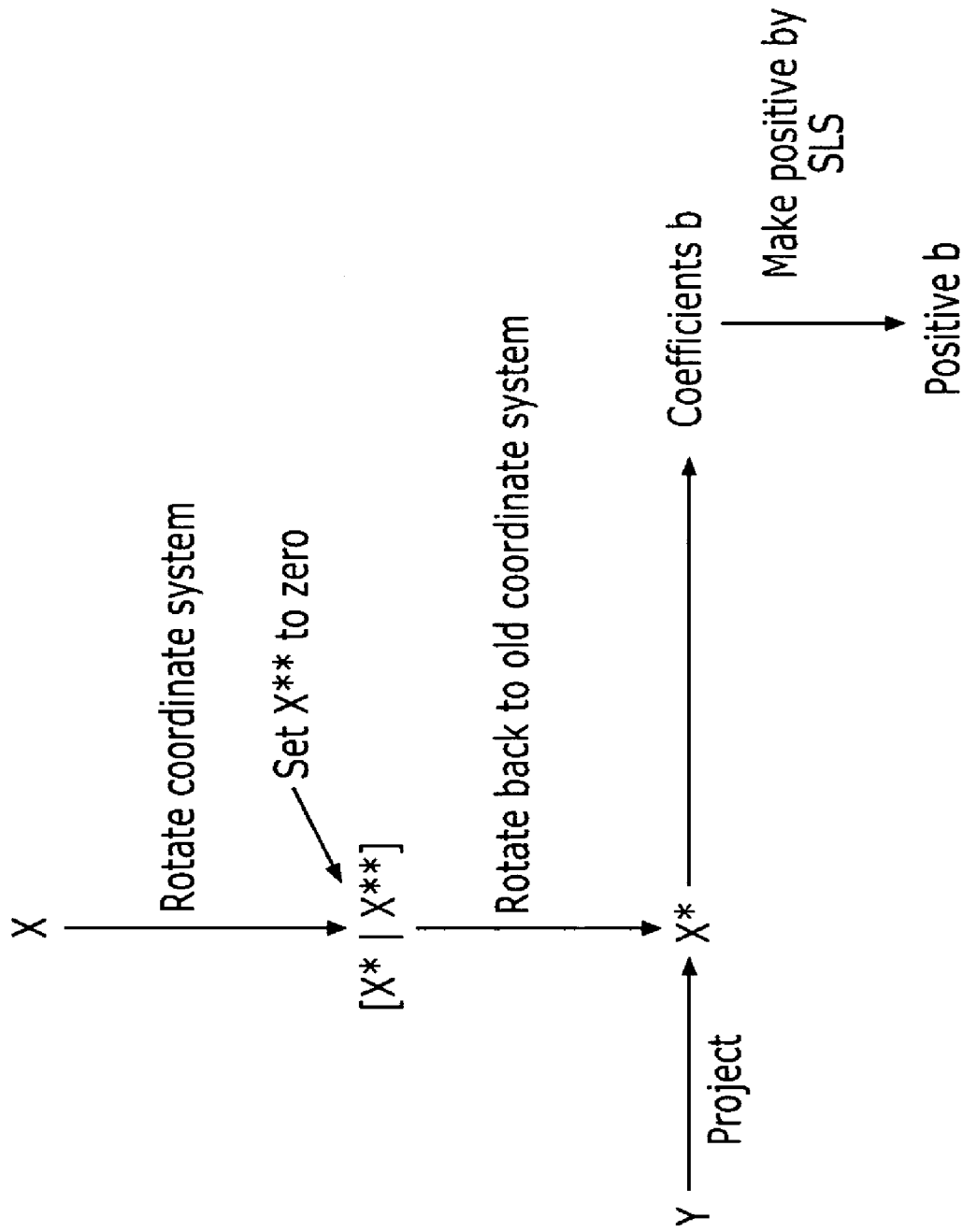
FIG. 5 is a schematic diagram of an interrogation protocol used to evaluate signal data for composite spectra having contributions from overlapping constituents according to embodiments of the present invention.

FIG. 5 is a schematic illustration of certain embodiments of the deconvolution operations used to evaluate closely correlated signal data. As shown, a design matrix "X" of constituent data comprising a plurality of individual mathematical data sets, each constituent data set including amplitude values of a respective spectrum lineshape of a selected constituent parameter over the variable space, spectrum length, or data points of interest, is obtained. The coordinate system of the design matrix is rotated to generate a rotated design matrix "Z" and, ultimately, a reduced design matrix "X*" (and a related transposed matrix "X**"). The line extending between X* and X** represents a classifier or acceptance function that determines what principal component data in X will be excluded from X*. The matrix is then rotated back to the original coordinate system, thereby generating a reduced design matrix "X*" with data from X modified by the analysis performed at the rotation of the coordinate system. The matrix of the composite spectrum lineshape data "Y" is projected onto X* and the weighting coefficients "b" calculated. A sequential least squares ("SLS") regression analysis is performed on the defined weighting coefficients to ensure that positive weighting coefficients are established. The operations may be iteratively repeated.

FIG. 6 is a block diagram of exemplary embodiments of data processing systems that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 6, the memory 314 may include several categories of software and data used in the data processing system 305: the operating system 352; the application programs 354; the input/output (I/O) device drivers 358; a deconvolution module 350; and the data 356. The deconvolution module 350 can include a fitting module with computer program code that rotates a design matrix of a priori constituent data and generates a reduced design matrix of selected principal components using an acceptance function (rotated back) to yield non-negative weighting factors for target constituents of interest in an unknown sample undergoing analysis.

In certain embodiments, the deconvolution fitting module can employ a shrinkage estimator. The acceptance function can use Eigen values and a classifier. The composite data of the unknown sample can be presented as a matrix that is projected onto the reduced design matrix to yield the weighting coefficients of the target constituents. The data 356 may include signal (constituent and/or composite spectrum lineshape) data 362 which may be obtained from a data or signal acquisition system 320. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 or WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and preferably include at least one application which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the deconvolution module 350 being an application program in FIG. 6, as will be appreciated by those of skill in the art, other configurations may also be utilized while still benefiting from the teachings of the present invention. For example, the deconvolution module 350 may also be incorporated into the operating system 352, the I/O device drivers 358 or other such logical division of the data processing system 305. Thus, the present invention should not be construed as limited to the configuration of FIG. 6, which is intended to encompass any configuration capable of carrying out the operations described herein.

In certain embodiments, the deconvolution module 350 includes computer program code for generating a shrinkage estimator and defining an optimum weighting factor for a plurality of different selected constituents in complex samples having a plurality of closely correlated constituents that contribute to a composite signal. The computer program code can include a sequential least squares regression analysis based on a statistical model comprising: (a) a mathematical composite matrix representing spectrum measurements of the amplitude of a composite signal of an unknown sample across "n" points in the spectrum; and (b) a design matrix including respective mathematical matrices for the amplitude of each of a plurality of individual selected constituents across "n" points in the spectrum. The shrinkage estimator and acceptance function can be used to generate optimum weighting factors "$b_{opt}$" for each constituent of interest based on the difference between the composite signal amplitude and the constituent amplitudes defined by interrogation of the values in the constituent and composite vectors. The analysis can be iteratively repeated in a sequential least squares regression model until target or selected constituents have been assigned non-negative weighting factors such that a sequential least squares statistical evaluation produces a satisfactory non-negative solution set for the target constituents.

The I/O data port can be used to transfer information between the data processing system 305 and the image scanner or acquisition system 320 or another computer system or a network (e.g., the Internet) or to other devices controlled by the processor. These components may be conventional components such as those used in many conventional data processing systems, which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 6 but is intended to encompass any configuration capable of carrying out the operations described herein.

More particularly described, in particular embodiments, a target sample to be analyzed may have a number of different selected parts or constituents or individual or groupings of selected constituents. The number of constituent parts may be noted as k. Thus, a sample undergoing analysis can include constituent parts, $P_1, \ldots, P_k$. As noted above, the number k may be at least 10, and can be between 35-40 or even larger. The sample can be analyzed on a desired suitable analytical instrument, with the amplitude of the independent variable (e.g., intensity, wavelength, retention time, current, etc., as described above) varied. The amplitude or value of the independent constituent(s) varies corresponding to the detector response of the analytical instrument and the variation can be recorded in the form of a spectrum. The spectrum or lineshape consists of amplitude measurements (that may be intensity measurements in certain embodiments) at n points. These amplitude measurements of the sample being analyzed are stored in a composite matrix, Y.

Also, each constituent part, $P_j$, j=1 to k, is separately analyzed to define a standard or reference over the same independent variable space, region, or data points as the sample undergoing analysis. Each set of the respective reference constituent spectral amplitudes (such as intensities) are stored in a matrix $X_j$, where, j=1, . . . , k, also of length n. Thus, a design constituent matrix X can be represented by:

$$X=[X_1, X_2, \ldots, X_k, Z] \qquad (14)$$

where Z is a matrix of amplitude data regarding at least one additional variable that can be deconvolved from the spectral signal. For example, Z may contain data representing spectral intensities of other known or unknown constituents, the imaginary part of the spectrum of the analyte sample (where Y contains the real part of that spectrum), noise, etc . . . . However, it is noted that Z can be a matrix, a vector, or, in certain embodiments, even null (a degenerate form of matrix with 0 columns).

In certain embodiments, Z is a matrix of size n×w, where w≧0. In certain particular embodiments, w=1. The estimated contributions of the individual components to the sample or analyte composite spectrum can be found by determining a normalized or optimal coefficient weightings $b_{opt}$ given by equation 15. The normalized weighting coefficient minimizes the values inside the brackets of the arg $\min_b$ function.

$$b_{opt} = \arg\min_b\{\|Y-Xb\|:b\geq 0\}. \quad (15)$$

These normalized weightings can be found by solving equation (15) using a shrinkage estimator to the regression problem, followed by the application of non-negative least squares to ensure that the non-negativity constraint is satisfied. The cycle is repeated until the least squares solution provides only non-negative weighting factors. The shrinkage estimator can be based on the spectral decomposition of the matrix $M=X^TX$ where $X^T$ represents a transposition of the constituent matrix X. Further, the spectral decomposition matrix M may be expressed by the following:

$$M = Q\Lambda Q^T \quad (16)$$

where Q (k+w)×(k+w) is orthogonal, and Λ(k+w)×(k+w) is a diagonal matrix comprising eigenvalues. The eigenvalue matrix Λ is sorted with the largest eigenvalue in the (1,1) element or position, the next largest value in the (2,2) element or position, and continuing left to right and top to bottom, etc., until the smallest element is placed in the (n, n) element or position. An adjustable tolerance parameter "τ" can be defined such that τ≧0. Also an acceptance or classifier function "A" can be defined such that A(λ): ℜ→{0, 1} which indicates which component is accepted into a fitting model.

A reduced eigenvalue matrix "$\Lambda_{red}$" can be defined as:

$$\Lambda_{red} = \Lambda\mathrm{diag}(A(\Lambda_{j,j})) \quad (17)$$

The X* matrix ("reduced design matrix") described above may be identified as:

$$X^* = Q\,\Lambda_{red}^{1/2} \quad (18)$$

One acceptance function that has been used is:

$$A(\lambda) = \begin{cases} 1 & \text{if } \lambda > \tau\Lambda_{1,1} \\ 0 & \text{otherwise} \end{cases} \quad (19)$$

where τ has been chosen to minimize Var b while maintaining E{b}. Examples of values for τ are in the range between $10^{-6}$ and $4\times10^{-6}$ for cases where k is about 37, i.e., where there are about 37 constituents or parts "$P_1$-$P_{37}$". Other values may be appropriate for lesser or greater numbers of constituents. Then b can be calculated as:

$$b = Q\Lambda_{red}^{-1}Q^TX^TY \quad (20)$$

C. Configuration of Exemplary System for Acquiring and Calculating Lineshape

Referring now to FIG. 7, a system 7 for acquiring and calculating the lineshape of a selected sample is illustrated. The system 7 includes an NMR spectrometer 10 for taking NMR measurements of a sample. In one embodiment, the spectrometer 10 is configured so that the NMR measurements are conducted at 400 MHz for proton signals; in other embodiments the measurements may be carried out at 360 MHz or other desired frequency. Other frequencies corresponding to a desired operational field strength may also be employed. Typically, a proton flow probe is installed, as is a temperature controller to maintain the sample temperature at 47+/−0.2 degrees C. Field homogeneity of the spectrometer 10 can be optimized by shimming on a sample of 99.8% $D_2O$ until the spectral linewidth of the HDO NMR signal is less than 0.6 Hz. The 90° RF excitation pulse width used for the $D_2O$ measurement is typically ca. 6-7 microseconds.

Referring again to FIG. 7, the spectrometer 10 is controlled by a digital computer 11 or other signal processing unit. The computer 11 should be capable of performing rapid Fourier transformations and may include for this purpose a hard-wired sine table and hardwired multiply and divide circuit. It may also include a data link 12 to an external personal computer 13, and a direct-memory-access channel 14 which connects to a hard disc unit 15.

The digital computer 11 may also include a set of analog-to-digital converters, digital-to-analog converters and slow device I/O ports which connect through a pulse control and interface circuit 16 to the operating elements of the spectrometer. These elements include an RF transmitter 17 which produces an RF excitation pulse of the duration, frequency and magnitude directed by the digital computer 11, and an RF power amplifier 18 which amplifies the pulse and couples it to the RF transmit coil 19 that surrounds sample cell 20. The NMR signal produced by the excited sample in the presence of a 9.4 Tesla polarizing magnetic field produced by superconducting magnet 21 is received by a coil 22 and applied to an RF receiver 23. The amplified and filtered NMR signal is demodulated at 24 and the resulting quadrature signals are applied to the interface circuit 16 where they are digitized and input through the digital computer 11 to a file in the disc storage 15. The deconvolving module 350 (FIG. 6) can be located in the digital computer 11 and/or in a secondary computer that may be on-site or remote.

After the NMR data are acquired from the sample in the measurement cell 20, processing by the computer 11 produces another file that can, as desired, be stored in the disc storage 15. This second file is a digital representation of the chemical shift spectrum and it is subsequently read out to the computer 13 for storage in its disc storage 25. Under the direction of a program stored in its memory, the computer 13, which may be personal, laptop, desktop, or other computer, processes the chemical shift spectrum in accordance with the teachings of the present invention to print a report, which is output to a printer 26 or electronically stored and relayed to a desired email address or URL. Those skilled in this art will recognize that other output devices, such as a computer display screen, may also be employed for the display of results.

It should be apparent to those skilled in the art that the functions performed by the computer 13 and its separate disc storage 25 may also be incorporated into the functions performed by the spectrometer's digital computer 11. In such case, the printer 26 may be connected directly to the digital computer 11. Other interfaces and output devices may also be employed, as are well-known to those skilled in this art.

The invention will now be described in more detail in the following non-limiting examples.

EXAMPLE 1

Acquisition of Sample Lineshape Data

Sample lineshape data is obtained from the analysis method of interest. One example is acquiring blood or blood plasma sample NMR lineshape data as described above for measurement of exemplary reference samples. The same field-strength NMR spectrometer is used (typically 400 MHz) and it is set up to operate in the identical fashion used to acquire the lipoprotein reference spectra. Other frequencies and magnetic fields may be employed. The time domain spectrum (FID) of the plasma sample is acquired in the identical fashion as the reference spectra, except that 2-transient spectra of up to 5 multiplicates are acquired rather than a single 32-transient or higher spectrum. Processing is carried out in an identical manner to produce a digitized representation of the blood plasma sample spectrum in the disk of the computer. The whole plasma spectrum is then accurately referenced to the sharp NMR resonance peak produced by the calcium complex of EDTA which is present in the sample. The sample spectrum and the reference spectra are shifted as needed to align the CaEDTA peak at 2.519 ppm on the horizontal scale. It is noted that operations of the invention can also be carried out for spectral alignment processing of alternate internal reference signals. For example, operations of the present invention can be carried out for internal references such as, but not limited to, glucose or lactate signals that can be used for spectral alignment purposes. Other analysis methods as well as other signal acquisition techniques can be employed, depending on the application, as will be appreciated by those of skill in the art.

Precision Study

Figure 8:
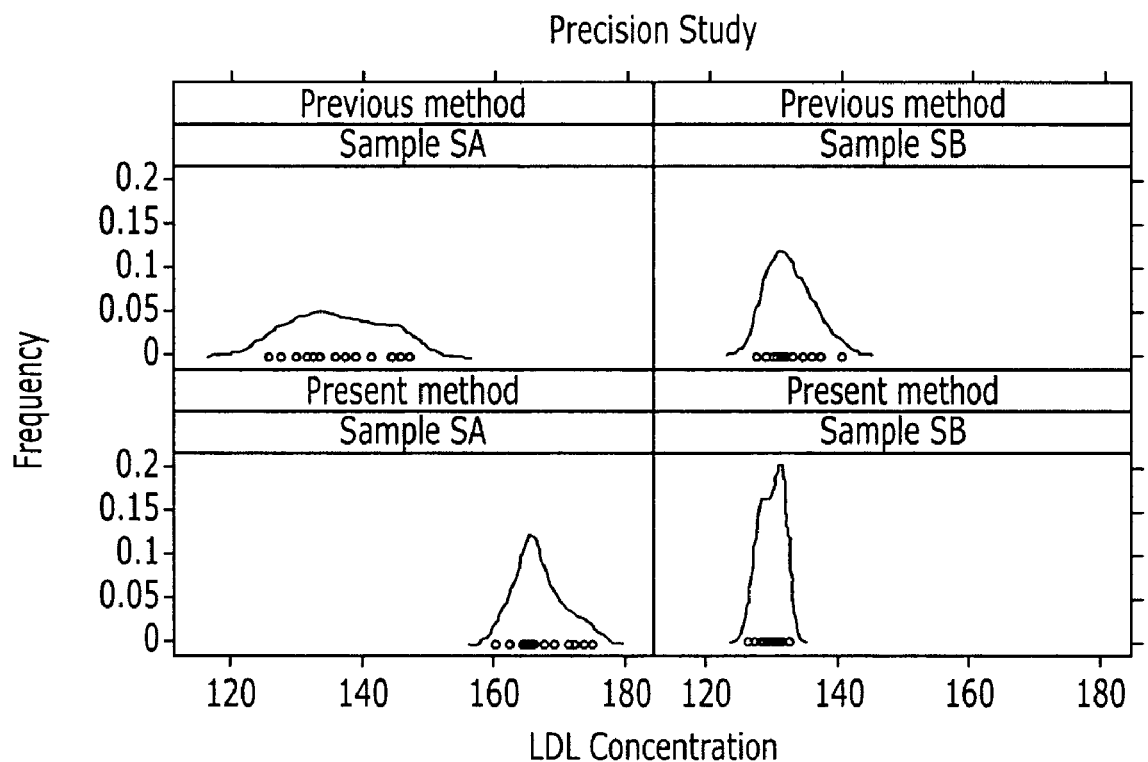
FIG. 8 is a graph of the distribution of repeated NMR-derived measurements of LDL concentration taken on sample SA and sample SB analyzed according to operations of the present invention compared to conventional processing method.

Two samples, SA and SB, were repeatedly analyzed on several NMR instruments. Lipoprotein information was generated for each result for both the improved deconvolution method and the conventional or standard deconvolution method. FIG. 8 illustrates the distribution of replicate measurements for samples SA and SB under both algorithms for LDL cholesterol concentrations. The coefficient of variation ("CV") for each algorithm is shown in Table 1 and illustrates reproducibility measures of a given sample when repeatedly interrogated.

TABLE 1

| Sample | Algorithm | N | Spread CV | CV Ratio |
|---|---|---|---|---|
| SA | Present method | 24 | 2.19 | |
|    | Previous method | 24 | 4.82 | 0.45 |
| SB | Present method | 24 | 1.28 | |
|    | Previous method | 24 | 2.41 | 0.53 |

In Table 1, CV=coefficient of variation expressed as a percentage. CV Ratio is the ratio in CV between the improved method and the previous or conventional method used in the past.

Randomly Selected Samples

The spectra from a set of 595 randomly selected plasma samples were analyzed using both the improved method described above and the previous method. The spectra of each sample was measured 5 times, and the variability among these five measurements was then characterized. Because this is a much larger selection of plasma samples than in the precision study, a wider variety of lipoprotein profiles can be encountered.

Figure 9:
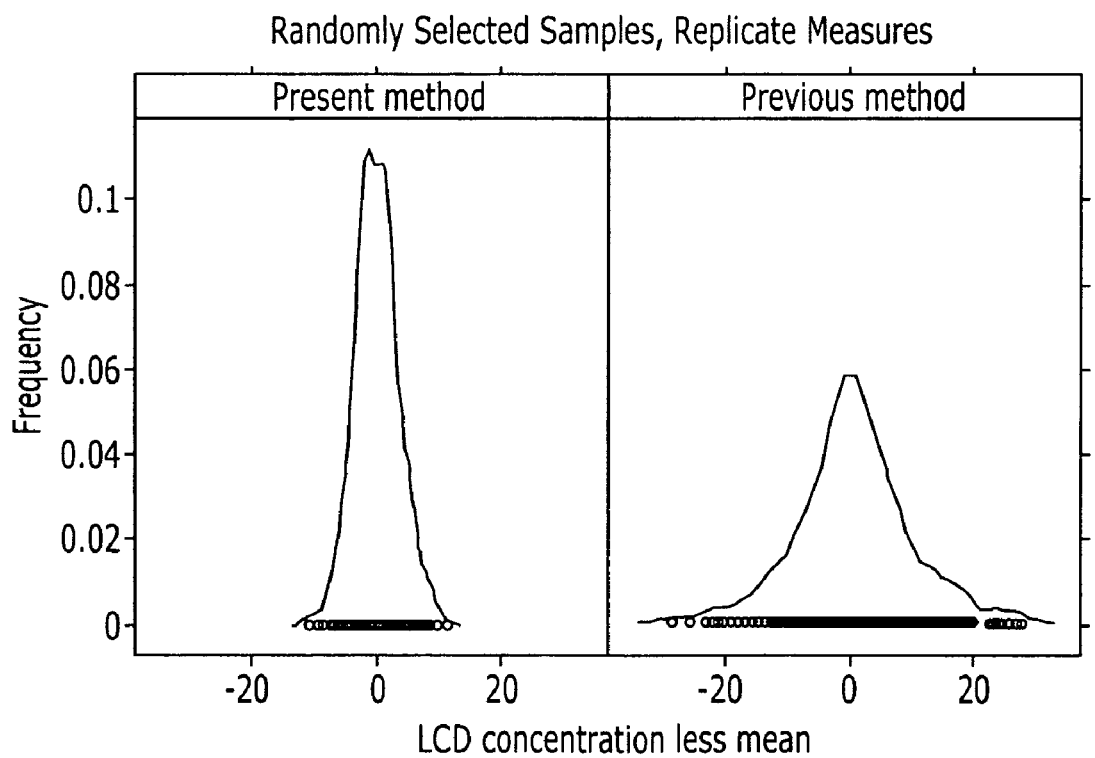
FIG. 9 is a graph of the distribution of a study of the distribution of repeated NMR-derived LDL concentration measurements of over five hundred different samples analyzed according to the operations provided by the present invention and the conventional processing method.

The difference in the LDL concentration and the mean LDL concentration for a given subject were computed, and these differences were then plotted. Because each subject's results now have the same mean of zero, all subjects can be plotted on the same graph. FIG. 9 illustrates the distribution of LDL concentrations (centered at zero) for both fitting methods. FIG. 9 is a graph of the variability (or reproducibility) from repeatedly measured spectra in 595 randomly selected samples. For each subject, the five measurements were used to compute deviation for that subject and algorithm, with smaller deviations being better.

It is believed that while the previous method produces results that are at least as good as other clinical evaluation techniques, the improved method is able to reduce variability and improve on the reproducibility of measurements. The within sample coefficient of variation for the improved method for LDL measurements in the data obtained is 2.34% (median) and 6.32% (median) for the prior method. Thus, the new method can reduce the variability by over 50%, and as shown in Table 2, can reduce the variability by about 63% (median value). See Table 2.

TABLE 2

Distribution of standard deviations within samples, by algorithm.

| | Distribution of within sample CV | | | | |
|---|---|---|---|---|---|
| | Min | Q1 | Median | Q3 | Max |
| Current | 0.81% | 1.66% | 2.34% | 3.16% | 7.52% |
| Previous | 1.13% | 3.93% | 6.32% | 9.14% | 17.66% |

Table 2 provides a measure of reproducibility using the coefficient of variation CV, where CV=SD/mean. For the constituent measured in this example, SD is proportional to the mean in this application, at least for LDL concentration, the CV value is a characterization of variability.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

The invention claimed is:

1. A method for determining the presence of and/or a measurement for a plurality of constituents in a composite signal extending about a spectrum of interest obtained from a target sample undergoing analysis, comprising:

generating a mathematical design matrix of constituent data comprising a plurality of selected individual mathematical constituent matrix data sets, each constituent matrix data set including constituent amplitude values of a respective spectrum lineshape of a selected independent parameter over a desired number of data points of a known reference sample that is generated by a predetermined analysis method, the reference sample having a known concentration;

generating a composite mathematical matrix comprising a data set of amplitude values of a composite spectrum lineshape of the selected independent parameter over the desired number of data points for a target sample undergoing quantitative analysis that is generated by the predetermined analysis method, the composite lineshape comprising spectral contributions from a plurality of the selected individual constituents included in the design matrix;

rotating the design matrix to provide a rotated design matrix of principal components;

selectively excluding data corresponding to certain of the principal components in the rotated design matrix;

generating a reduced design matrix based on the steps of rotating and excluding;

computing regression fit weighting coefficients based on data in the reduced design matrix and the composite matrix for the plurality of individual constituents and multiplying the regression coefficients by the known concentration of the reference sample to generate a concentration value of at least one constituent and/or at least one group of constituents in the target sample; then electronically storing or outputting or storing and outputting the generated concentration value.

2. A method according to claim 1, wherein the computing step comprises a sequential least squares restraint in a statistical regression analysis to force the defined weighting coefficients of target constituents of interest to be positive.

3. A method according to claim 1, wherein the predetermined analysis method is NMR spectroscopy and the lineshapes correspond to intensity over a desired interval or region in a chemical shift spectrum such that intensity is the dependent parameter in the analysis.

4. A method according to claim 1, wherein the plurality of selected individual constituents comprise lipoproteins.

5. A method according to claim 1, wherein the design matrix includes columns and rows of data, wherein the number of columns in the design matrix corresponds to the number of different individual constituents of interest plus at least one additional column representing spectra contributions from at least one non-relevant variable.

6. A method according to claim 1, wherein the target sample is an in vitro biosample.

7. A method according to claim 1, wherein the target sample comprises blood plasma or serum.

8. A method according to claim 1, wherein the selectively excluding data corresponding to certain of the principal components in the rotated design matrix comprises interrogating the rotated design matrix using a defined acceptance function to find those rotated principal components with contributions that benefit the deconvolution, then rotating back those accepted principal components to form the reduced design matrix.

9. A method according to claim 1, wherein the electronically storing or outputting or storing and outputting the generated concentration value generates a clinical report of a plurality of generated concentration values of selected constituents and groups of constituents in the target sample.

10. A method for determining the presence of and/or a measurement for a plurality of constituents in a composite signal extending about a spectrum of interest obtained from a target sample undergoing analysis, comprising:

generating a mathematical design matrix of constituent data comprising a plurality of selected individual mathematical constituent matrix data sets, each constituent matrix data set including constituent amplitude values of a respective spectrum lineshape of a selected independent parameter over a desired number of data points of a known reference sample that is generated by a predetermined analysis method;

generating a composite mathematical matrix comprising a data set of amplitude values of a composite spectrum lineshape of the selected independent parameter over the desired number of data points for a target sample undergoing analysis that is generated by the predetermined analysis method, the composite lineshape comprising spectral contributions from a plurality of the selected individual constituents included in the design matrix;

rotating the design matrix to provide a rotated design matrix of principal components;

selectively excluding data corresponding to certain of the principal components in the rotated design matrix;

generating a reduced design matrix based on the steps of rotating and excluding;

computing regression fit weighting coefficients based on data in the reduced design matrix and the composite matrix for the plurality of individual constituents to determine the presence of and/or measurement of the selected constituents in the target sample; and outputting quantitative data regarding at least one selected constituent or at least one group of constituents in the target sample based on the computed regression fit weighting coefficients;

wherein the design matrix comprises at least 10 different constituent data sets, each representing a respective one of at least 10 different closely correlated chemical constituents, and wherein a plurality of the constituents have overlapping signal lineshapes in a region of the spectrum analyzed.

11. A method according to claim 10, wherein the quantitative data comprises clinically relevant concentration values of constituents and groups of constituents in the target sample, and wherein the outputting comprises providing the concentration values in a patient report.

12. A method for determining the presence of and/or a measurement for a plurality of constituents in a composite signal extending about a spectrum of interest obtained from a target sample undergoing analysis, comprising:

generating a mathematical design matrix of constituent data comprising a plurality of selected individual mathematical constituent matrix data sets, each constituent matrix data set including constituent amplitude values of a respective spectrum lineshape of a selected independent parameter over a desired number of data points of a known reference sample that is generated by a predetermined analysis method;

generating a composite mathematical matrix comprising a data set of amplitude values of a composite spectrum line shape of the selected independent parameter over the desired number of data points for a target sample undergoing analysis that is generated by the predetermined analysis method, the composite lineshape comprising spectral contributions from a plurality of the selected individual constituents included in the design matrix, wherein the plurality of selected individual constituents comprise at least 35 different individual lipoprotein constituents;

rotating the design matrix to provide a rotated design matrix of principal components;

selectively excluding data corresponding to certain of the principal components in the rotated design matrix;

generating a reduced design matrix based on the steps of rotating and excluding;

computing regression fit weighting coefficients based on data in the reduced design matrix and the composite matrix for the plurality of individual constituents to determine the presence of and/or measurement of the selected constituents in the target sample; then outputting a concentration value of at least one of the plurality of individual lipoprotein constituents and/or at least one related grouping of lipoprotein subclass constituents.

13. A method according to claim 12, wherein the outputting concentration values of at least one of the plurality of individual lipoprotein constituents and/or at least one of the plurality of related groupings of lipoprotein subclass constituents is carried out to provide a patient report of a respective concentration of a plurality of different related groupings of subclass lipoprotein constituents.

14. A method for determining the presence of and/or a measurement for a plurality of constituents in a composite signal extending about a spectrum of interest obtained from a target sample undergoing analysis, comprising:

generating a mathematical design matrix of constituent data comprising a plurality of selected individual mathematical constituent matrix data sets, each constituent matrix data set including constituent amplitude values of a respective spectrum lineshape of a selected independent parameter over a desired number of data points of a known reference sample that is generated by a predetermined analysis method, the reference sample having a known concentration;

generating a composite mathematical matrix comprising a data set of amplitude values of a composite spectrum lineshape of the selected independent parameter over the desired number of data points for a target sample undergoing quantitative analysis that is generated by the predetermined analysis method, the composite lineshape comprising spectral contributions from a plurality of the selected individual constituents included in the design matrix;

rotating the design matrix to provide a rotated design matrix of principal components;

selectively excluding data corresponding to certain of the principal components in the rotated design matrix;

generating a reduced design matrix based on the steps of rotating and excluding; and computing regression fit weighting coefficients based on data in the reduced design matrix and the composite matrix for the plurality of individual constituents;

multiplying the regression coefficients by the predetermined concentration of the known reference sample to generate a concentration value for at least constituent or at least one group of constituents in the target sample; then electronically storing or outputting or storing and outputting the at least one generated concentration value, wherein each column of data in the design matrix corresponds to a principal component, and wherein the step of generating a reduced design matrix is carried out by using a classifier function that reviews each principal component in the rotated design matrix and accepts columns of data corresponding to the respective principal component therein based on whether the principal component has a value that is determined to improve the deconvolution.

15. A method according to claim 14, wherein the electronically storing or outputting or storing and outputting the at least one generated concentration value comprises providing a quantitative test report of constituents and/or groups of constituents in the target sample to a user.

16. A method for determining the presence of and/or a measurement for a plurality of constituents in a composite signal extending about a spectrum of interest obtained from a target sample undergoing analysis, comprising:

generating a mathematical design matrix of constituent data comprising a plurality of selected individual mathematical constituent matrix data sets, each constituent matrix data set including constituent amplitude values of a respective spectrum lineshape of a selected independent parameter over a desired number of data points of a known reference sample that is generated by a predetermined analysis method, the reference sample having a known concentration;

generating a composite mathematical matrix comprising a data set of amplitude values of a composite spectrum lineshape of the selected independent parameter over the desired number of data points for a target sample undergoing analysis that is generated by the predetermined analysis method, the composite lineshape comprising spectral contributions from a plurality of the selected individual constituents included in the design matrix;

rotating the design matrix to provide a rotated design matrix of principal components;

selectively excluding data corresponding to certain of the principal components in the rotated design matrix;

generating a reduced design matrix based on the steps of rotating and excluding; and computing regression fit weighting coefficients based on data in the reduced design matrix and the composite matrix for the plurality of individual constituents;

multiplying the regression coefficients by the known concentration of the reference sample to generate a concentration value of at least one constituent and/or at least one group of constituents in the target sample; then electronically storing or outputting or storing and outputting the at least one generated concentration value, wherein the step of generating the reduced design matrix further comprises computing a normal equations matrix from the design matrix.

17. A method according to claim 16, wherein the design matrix comprises a number of columns "n", a respective one each for each principal component of interest, and wherein the step of generating the reduced design matrix further comprises interrogating the normal equations matrix by applying a predetermined acceptance function to the principal components in the rotated design matrix to accept and/or reject the interrogated data to generate the reduced design matrix, the reduced design matrix having a lesser number of columns than the design matrix.

18. A method according to claim 16, wherein the electronically storing or outputting or storing and outputting the at least one generated concentration value comprises providing a quantitative test report of constituents and/or groups of constituents in the target sample to a user.

19. A method for determining the presence of and/or a measurement for a plurality of constituents in a composite signal extending about a spectrum of interest obtained from a target sample undergoing analysis, comprising:

generating a mathematical design matrix of constituent data comprising a plurality of selected individual mathematical constituent matrix data sets, each constituent matrix data set including constituent amplitude values of a respective spectrum lineshape of a selected independent parameter over a desired number of data points of a known reference sample that is generated by a predetermined analysis method, the reference sample having a known concentration;

generating a composite mathematical matrix comprising a data set of amplitude values of a composite spectrum lineshape of the selected independent parameter over the desired number of data points for a target sample undergoing quantitative analysis that is generated by the predetermined analysis method, the composite lineshape comprising spectral contributions from a plurality of the selected individual constituents included in the design matrix;

rotating the design matrix to provide a rotated design matrix of principal components;

selectively excluding data corresponding to certain of the principal components in the rotated design matrix;

generating a reduced design matrix based on the steps of rotating and excluding;

computing regression fit weighting coefficients based on data in the reduced design matrix and the composite matrix for the plurality of individual constituents, wherein the step of computing regression fit weighting coefficients is carried out with the reduced design matrix in a non-rotated state; and multiplying the regression coefficients by the known concentration of the reference sample to generate a concentration value of at least one constituent or at least one group of constituents in the target sample; then electronically storing or outputting or storing and outputting the at least one generated concentration value.

20. A method according to claim 19, wherein the electronically storing or outputting or storing and outputting the at least one generated concentration value is carried out to provide a quantitative test report of a plurality of constituents in the target sample.

21. A computer program product for deconvolving the spectral contribution of a plurality of closely correlated constituents in a composite signal, the computer program product comprising:

a computer readable storage medium having computer readable program code embodied in said medium, said computer-readable program code comprising:

computer readable program code that generates a design matrix of individual selected constituent data sets for a plurality of different selected constituents in a spectrum of interest, each individual selected constituent data set including amplitude values of its associated spectral lineshape, wherein a plurality of the different selected constituents are closely correlated with overlapping signal lineshapes in the spectrum of interest;

computer readable program code that obtains a composite signal of a target sample undergoing analysis and generates a composite matrix of amplitude values of the lineshape of the composite signal in the spectrum of interest, the target sample comprising spectra from a plurality of the selected closely correlated constituents that contribute to the composite signal;

computer readable program code for rotating the design matrix;

computer readable program code that generates a reduced design matrix;

computer readable program code that computes regression fit weighting coefficients based on the design matrix, the reduced matrix, and the composite matrix to thereby deconvolve the spectral contribution of at least one non-target variable across the spectrum of interest in the composite signal;

computer readable program code that determines the presence of and/or measurement of at least one constituent in the target sample based on data from at least one of: (a) the regression fit weighting coefficients; and (b) the deconvolved spectral contribution of the at least one non-target variable; and computer readable program code that outputs data regarding at least one selected constituent and/or at least one group of constituents in the target sample based on a deconvolved spectral contribution of the plurality of closely correlated constituents in the composite signal.

22. A computer program product according to claim 21, further comprising computer readable program code for performing a sequential least squares analysis that evaluates the optimum weighting factors to restrain negative coefficients.

23. A computer program product according to claim 22, wherein the computer readable program code that generates the design matrix uses "n" columns, one column for each selected individual constituent of interest.

24. A computer program product according to claim 23, wherein the computer readable program code that generates the design matrix uses columns, one column for each selected individual constituent of interest, and at least one for a parameter that contributes to the amplitude of the composite lineshape signal but is not a target constituent of interest.

25. A computer program product according to claim 21, wherein the composite and constituent spectral signal lineshapes are NMR spectroscopic signals.

26. A computer program product according to claim 25, wherein the composite lineshape is obtained from a blood plasma or serum sample, and wherein the plurality of selected constituents comprise lipoprotein subclass constituents or related groupings thereof.

27. A computer product according to claim 21, wherein the computer readable program code that generates a reduced design matrix comprises computer program code that interrogates the rotated design matrix using a defined acceptance function to find those rotated principal components with contributions that benefit the deconvolution.

28. A computer program product for deconvolving the spectral contribution of a plurality of closely correlated constituents in a composite signal, the computer program product comprising:

a computer readable storage medium having computer readable program code embodied in said medium, said computer-readable program code comprising:

computer readable program code that generates a design matrix of individual selected constituent data sets for a plurality of different selected constituents in a spectrum of interest, each individual selected constituent data set including amplitude values of its associated spectral lineshape, wherein a plurality of the different selected constituents are closely correlated with overlapping signal lineshapes in the spectrum of interest, wherein the computer program code that generates the design matrix uses "n" columns, one column for each selected individual constituent of interest and at least one for a parameter that contributes to the amplitude of the composite lineshape signal but is not a target constituent of interest;

computer readable program code that obtains a composite signal of a target sample undergoing analysis and generates a composite matrix of amplitude values of the lineshape of the composite signal in the spectrum of interest, the target sample comprising spectra from a plurality of the selected closely correlated constituents that contribute to the composite signal;

computer readable program code for rotating the design matrix;

computer readable program code that generates a reduced design matrix;

computer readable program code that computes regression fit weighting coefficients based on the design matrix, the reduced matrix, and the composite matrix to thereby deconvolve the spectral contribution of at least one non-target variable across the spectrum of interest in the composite signal;

computer readable program code for performing a sequential least squares analysis that evaluates optimum weighting factors to restrain negative coefficients;

computer readable program code that determines the presence of and/or measurement of at least one constituent in the target sample based on data from at least one of: (a) the regression fit weighting coefficients; and (b) the deconvolved spectral contribution of the at least one non-target variable; and computer readable program code that outputs data regarding at least one selected constituent and/or at least one selected group of constituents in the target sample based on the deconvolved spectral contribution of the plurality of closely correlated constituents in the composite signal, wherein the computer readable program code that generates the reduced design matrix includes computer readable program code that interrogates the rotated design matrix and uses a predetermined classifier function to selectively include and reject data in the rotated design matrix from the reduced design matrix.

29. A computer program product for deconvolving the spectral contribution of a plurality of closely correlated constituents in a composite signal, the computer program product comprising:

a computer readable storage medium having computer readable program code embodied in said medium, said computer-readable program code comprising:

computer readable program code that generates a design matrix of individual selected constituent data sets for a plurality of different selected constituents in a spectrum of interest, each individual selected constituent data set including amplitude values of its associated spectral lineshape, wherein a plurality of the different selected constituents are closely correlated with overlapping signal lineshapes in the spectrum of interest;

computer readable program code that obtains a composite signal of a target sample undergoing analysis and generates a composite matrix of amplitude values of the lineshape of the composite signal in the spectrum of interest, the target sample comprising spectra from a plurality of the selected closely correlated constituents that contribute to the composite signal;

computer readable program code for rotating the design matrix;

computer readable program code that generates a reduced design matrix; and computer readable program code that computes regression fit weighting coefficients based on the design matrix, the reduced matrix, and the composite matrix to thereby deconvolve the spectral contribution of at least one non-target variable across the spectrum of interest in the composite signal;

computer readable program code for performing a sequential least squares analysis that evaluates optimum weighting factors to restrain negative coefficients wherein the design matrix includes columns of constituent data, each column associated with a principal component, and wherein the computer program code that generates the reduced design matrix comprises:

computer readable program code that: (a) computes a normal equations matrix from the design matrix; and (b) interrogates the normal equations matrix by applying a predetermined classifier function to selectively include and reject data associated with certain of the principal components in the rotated design matrix from the reduced design matrix;

computer readable program code that deconvolves the composite signal and determines the presence of and/or measurement of at least one constituent in the target sample based on data from at least one of: (a) the design matrix; and (b) the reduced design matrix; and computer readable program code that outputs concentrations of selected constituents and/or selected groups of constituents in the target sample based on the deconvolved spectral contribution of the plurality of closely correlated constituents in the composite signal.

30. A computer program product for deconvolving the spectral contribution of a plurality of closely correlated constituents in a composite signal, the computer program product comprising:

a computer readable storage medium having computer readable program code embodied in said medium, said computer-readable program code comprising:

computer readable program code that generates a design matrix of individual selected constituent data sets for a plurality of different selected constituents in a spectrum of interest, each individual selected constituent data set including amplitude values of its associated spectral lineshape, wherein a plurality of the different selected constituents are closely correlated with overlapping signal lineshapes in the spectrum of interest;

computer readable program code that obtains a composite signal of a target sample undergoing analysis and generates a composite matrix of amplitude values of the lineshape of the composite signal in the spectrum of interest, the target sample comprising spectra from a plurality of the selected closely correlated constituents that contribute to the composite signal;

computer readable program code for rotating the design matrix;

computer readable program code that generates a reduced design matrix;

computer readable program code that computes regression fit weighting coefficients based on the design matrix, the reduced matrix, and the composite matrix to thereby deconvolve the spectral contribution of at least one non-target variable across the spectrum of interest in the composite signal;

computer readable program code that iteratively repeats a sequential least squares regression model using the design matrix, the reduced design matrix, and the composite matrix until selected target constituents of interest have been assigned non-negative weighting factors such that a sequential least squares statistical evaluation produces a non-negative solution set therefore; and computer readable program code that outputs data regarding selected constituents in the target sample based on the deconvolved spectral contribution of the plurality of closely correlated constituents in the composite signal.

31. A method of deconvolving a complex signal to evaluate an in vitro biosample, comprising:

(a) obtaining a plurality of individual NMR spectrum reference signals of selected target constituents of interest in an in vitro biosample;

(b) obtaining a composite NMR spectrum signal of the in vitro biosample taken from a subject for analysis, the composite signal including spectral contributions from a plurality of the individual target constituents of interest;

(c) generating a design matrix of individual data sets of the amplitude of the respective reference constituents in the NMR spectrum, the design matrix having columns or rows of data that correspond to principal components that contribute to the spectral lineshape of the composite signal;

(d) rotating the design matrix;

(e) generating a reduced design matrix of principal component data by selectively excluding principal components that do not improve the estimation of the target constituents in the composite signal;

(f) deriving regression fit weighting coefficients for the selected target constituents in the composite signal;

(g) generating a calculated composite lineshape for the sample, the calculated lineshape being calculated based on the derived weighting coefficients of respective constituent reference spectrums of constituents potentially present in the sample, (h) determining the presence or absence of and/or the level or concentration of at least one selected constituent in the sample based on the calculated composite lineshape; and (i) outputting data corresponding to the determined presence or absence of and/or the level or concentration of at least one selected constituent in the sample.

32. A method according to claim 31, wherein the biosample is a blood, blood plasma, or serum sample.

33. A method according to claim 32, wherein the constituents of interest are lipids and/or lipoproteins.

34. A method according to claim 33, wherein the reference spectra for the plurality of lipoprotein constituents includes spectra for a plurality of different lipoprotein subclasses.

35. A method according to claim 34, further comprising the step of producing a customized subject report listing the concentrations of the lipoprotein constituents present in the sample.

36. A method according to claim 31, further comprising, after step (f), applying a sequential least squares analysis to restrain negative coefficients to zero until the target constituent or constituents of interest are non-negative.

37. A method according to claim 31, further comprising obtaining an internal reference signal and aligning the reference spectra and the sample spectra based on the internal reference signal.

38. A method according to claim 37, wherein the internal reference signal is derived from at least one NMR resonance peak produced by lactate.

39. A method according to claim 38, wherein the internal reference signal is derived from at least one NMR resonance peak produced by glucose.

40. A method according to claim 31, wherein step (e) generating a reduced design matrix of principal component data by selectively excluding principal components that do not improve the estimation of the target constituents in the composite signal comprises interrogating the rotated design matrix using a defined acceptance function to find those rotated principal components with contributions that benefit the deconvolution.

41. An apparatus for measuring lipoprotein constituents in a subject, comprising:

an NMR spectrometer for acquiring an NMR composite spectrum of a blood plasma or serum sample; and a computer readable storage medium having computer readable program code embodied in the medium in communication with the NMR spectrometer, the computer-readable program code comprising:

computer readable program code configured to define a plurality of individual NMR constituent spectrums, each associated with a selected reference lipoprotein constituent signal lineshape, each constituent spectrum having associated spectra that contribute to the composite NMR spectrum of the blood plasma or serum sample;

computer readable program code configured to generate a design matrix of the selected individual constituents, the design matrix including data sets for each of the plurality of individual lipoprotein constituents in a spectrum of interest, each individual selected constituent data set including amplitude values of its associated spectral lineshape, wherein a plurality of the selected individual constituents are closely correlated with overlapping signal lineshapes in the spectrum of interest;

computer readable program code configured to obtain a composite signal of a target sample undergoing analysis and generates a composite matrix of amplitude values of the line shape of the composite signal in the spectrum of interest, the target sample comprising spectra from a plurality of the selected individual constituents that contribute to the composite signal;

computer readable program code configured to rotate the design matrix;

computer readable program code configured to generate a reduced design matrix;

computer readable program code configured to compute regression fit weighting coefficients based on the design matrix, the reduced matrix, and the composite matrix to deconvolve the spectral contribution of at least one non-target variable across the spectrum of interest in the composite signal;

computer readable program code configured to apply a sequential least squares analysis to the regression fit weighting coefficients to restrain negative coefficients to zero;

computer readable program code configured to determine a calculated composite lineshape based on the weighting coefficients;

computer readable program code configured to determine the concentrations of the lipoprotein constituents and/or at least one group of lipoprotein constituents in the sample undergoing analysis; and computer readable program code configured to generate a report with the determined concentrations.

42. An apparatus according to claim 41, wherein the computer readable program code configured to generate a reduced design matrix comprises computer program code that interrogates the rotated design matrix using a defined acceptance function to find those rotated principal components with contributions that benefit the deconvolution.

43. An apparatus for determining the presence of and/or a measurement for a plurality of constituents in a composite signal extending about a spectrum of interest obtained from a target sample undergoing analysis, comprising:

means or generating a mathematical design matrix of constituent data comprising a plurality of selected individual mathematical constituent matrix data sets, each constituent matrix data set including constituent amplitude values of a respective spectrum lineshape of a selected independent parameter over a desired number of data points of a known reference sample that is generated by a predetermined analysis method;

means for generating a composite mathematical matrix comprising a data set of amplitude values of a composite spectrum lineshape of the selected independent parameter over the desired number of data points for a target sample undergoing analysis that is generated by the predetermined analysis method, the composite lineshape comprising spectral contributions from a plurality of the selected individual constituents included in the design matrix;

means for rotating the design matrix to provide a rotated design matrix of principal components;

means for selectively excluding data corresponding to certain of the principal components in the rotated design matrix;

means for generating a reduced design matrix based on the steps of rotating and excluding;

means for computing regression fit weighting coefficients based on data in the reduced design matrix and the composite matrix for the plurality of individual constituents to determine the presence of and/or measurement of the selected constituents in the target sample; and means for outputting or electronically storing or outputting and electronically storing concentration values of selected constituents and/or selected groups of constituents in the target sample.

44. An apparatus according to claim 43, wherein the means for computing employs a sequential least squares restraint in a statistical regression analysis to force the defined weighting coefficients of target constituents of interest to be positive.

45. An apparatus for determining the presence of and/or a measurement for a plurality of constituents in a composite signal extending about a spectrum of interest obtained from a target sample undergoing analysis, comprising:

means or generating a mathematical design matrix of constituent data comprising a plurality of selected individual mathematical constituent matrix data sets, each constituent matrix data set including constituent amplitude values of a respective spectrum lineshape of a selected independent parameter over a desired number of data points of a known reference sample that is generated by a predetermined analysis method;

means for generating a composite mathematical matrix comprising a data set of amplitude values of a composite spectrum lineshape of the selected independent parameter over the desired number of data points for a target sample undergoing analysis that is generated by the predetermined analysis method, the composite lineshape comprising spectral contributions from a plurality of the selected individual constituents included in the design matrix;

means for rotating the design matrix to provide a rotated design matrix of principal components;

means for selectively excluding data corresponding to certain of the principal components in the rotated design matrix;

means for generating a reduced design matrix based on the steps of rotating and excluding;

means for computing regression fit weighting coefficients based on data in the reduced design matrix and the composite matrix for the plurality of individual constituents to determine the presence of and/or measurement of the selected constituents in the target sample; and means for outputting or electronically storing or outputting and electronically storing concentration values of selected constituents, and/or selected groups of constituents in the target sample, wherein the design matrix comprises at least 10 different constituent data sets, each representing a respective one of at least 10 different closely correlated chemical constituents, and wherein a plurality of the constituents have overlapping signal line shapes in a region of the spectrum analyzed.

* * * * *

UNITED STATES PATENT AND TRADEMARK OFFICE
CERTIFICATE OF CORRECTION

PATENT NO. : 7,243,030 B2 Page 1 of 1
APPLICATION NO. : 10/691103
DATED : July 10, 2007
INVENTOR(S) : Reeve et al.

It is certified that error appears in the above-identified patent and that said Letters Patent is hereby corrected as shown below:

In The Claims:

Column 28, Claim 24, Line 40: Should read as
--the design matrix uses "n" columns, one column for each--

Signed and Sealed this

Twenty-third Day of October, 2007

JON W. DUDAS
*Director of the United States Patent and Trademark Office*